(12) United States Patent
Swarup et al.

(10) Patent No.: US 10,939,969 B2
(45) Date of Patent: Mar. 9, 2021

(54) COMMAND SHAPING TO DAMPEN VIBRATIONS IN MODE TRANSITIONS

(71) Applicant: INTUITIVE SURGICAL OPERATIONS, INC., Sunnyvale, CA (US)

(72) Inventors: Nitish Swarup, Sunnyvale, CA (US); David W. Robinson, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 208 days.

(21) Appl. No.: 16/204,449

(22) Filed: Nov. 29, 2018

(65) Prior Publication Data

US 2019/0090968 A1 Mar. 28, 2019

Related U.S. Application Data

(63) Continuation of application No. 15/125,944, filed as application No. PCT/US2015/020875 on Mar. 17, 2015, now Pat. No. 10,201,390.

(Continued)

(51) Int. Cl.
*A61B 34/00* (2016.01)
*A61B 34/30* (2016.01)
(Continued)

(52) U.S. Cl.
CPC .............. *A61B 34/30* (2016.02); *A61B 34/35* (2016.02); *A61B 34/37* (2016.02); *A61B 34/76* (2016.02);
(Continued)

(58) Field of Classification Search
CPC ......... A61B 34/30; A61B 34/76; A61B 34/35; A61B 34/37; A61B 2034/743;
(Continued)

(56) References Cited

U.S. PATENT DOCUMENTS

| | | |
|---|---|---|
| 5,184,601 A | 2/1993 | Putman et al. |
| 5,445,166 A | 8/1995 | Taylor et al. |

(Continued)

FOREIGN PATENT DOCUMENTS

| | | |
|---|---|---|
| CN | 101779979 A | 7/2010 |
| EP | 1815950 A1 | 8/2007 |

OTHER PUBLICATIONS

International Search Report and Written Opinion for Application No. PCT/US15/20875, dated Jun. 18, 2015, 12 pages.

(Continued)

*Primary Examiner* — Ian Jen
(74) *Attorney, Agent, or Firm* — Artegis Law Group, LLP

(57) ABSTRACT

Systems and methods are provided for the elimination/mitigation of vibration arising from a mode transition during robotic operation include a moveable robotic mechanism and a processor configured to control the robotic mechanism. The processor is configured to detect a request for a mode transition, wherein the request for the mode transition designates a new mode that is different than a current mode, determine initial parameters of the robotic mechanism, calculate a smoothing curve, and move the robotic mechanism according to the smoothing curve. The initial parameters include a position and a velocity of the robotic mechanism. The smoothing curve transitions between the current mode and the new mode and is C3 continuous. In some embodiments, to calculate the smoothing curve, the processor is configured to establish a first command position, calculate a (Continued)

step value, and set a second command position based on the first command position and the step value.

20 Claims, 17 Drawing Sheets

Related U.S. Application Data

(60) Provisional application No. 61/993,961, filed on May 15, 2014, provisional application No. 61/954,459, filed on Mar. 17, 2014.

(51) Int. Cl.
*A61B 34/37* (2016.01)
*A61B 34/35* (2016.01)

(52) U.S. Cl.
CPC ......... *A61B 34/74* (2016.02); *A61B 2034/304* (2016.02); *A61B 2034/305* (2016.02); *A61B 2034/742* (2016.02); *A61B 2034/743* (2016.02)

(58) Field of Classification Search
CPC ........ A61B 2034/304; A61B 2034/305; A61B 34/74; A61B 2034/742
See application file for complete search history.

(56) References Cited

U.S. PATENT DOCUMENTS

| | | | |
|---|---|---|---|
| 5,800,423 A | 9/1998 | Jensen et al. | |
| 5,808,665 A | 9/1998 | Green et al. | |
| 5,855,583 A | 1/1999 | Wang et al. | |
| 6,246,200 B1 | 6/2001 | Blumenkranz et al. | |
| 6,676,669 B2 | 1/2004 | Charles et al. | |
| 6,702,805 B1 | 3/2004 | Stuart et al. | |
| 6,758,843 B2 | 7/2004 | Jensen et al. | |
| 6,788,018 B1 | 9/2004 | Blumenkranz et al. | |
| 7,594,912 B2 | 9/2009 | Cooper et al. | |
| 7,689,320 B2 | 3/2010 | Prisco et al. | |
| 7,763,015 B2 | 7/2010 | Cooper et al. | |
| 8,649,905 B2 | 2/2014 | Ortmaier | |
| 2008/0292125 A1* | 11/2008 | Asnes .................. | H04R 25/606 381/326 |
| 2011/0276179 A1 | 11/2011 | Banks et al. | |
| 2012/0143212 A1 | 6/2012 | Madhani et al. | |
| 2013/0151009 A1 | 6/2013 | Okazaki | |
| 2016/0338751 A1* | 11/2016 | Kellar .................. | A61F 2/4607 |
| 2017/0071680 A1 | 3/2017 | Swarup et al. | |

OTHER PUBLICATIONS

Ohnishi K., et al., "Motion Control for Advanced Mechatronics," IEEE/ASME Transactions on Mechatronics, IEEE Service Center, Piscataway, NJ, US, vol. 1 (1), Mar. 1, 1996 (Mar. 1, 1996), pp. 56-67, XP000588547, ISSN: 1083-4435, DOI: 10.1109/3516. 491410.

Rivera-Guillen J.R., et al., "Methodology for Obtaining C3 Continuity on Tool Trajectory Featuring Acceleration and Jerk Constraint on Computer Numerical Control Machine," Journal of Mechanical Engineering Science, Dec. 2011, vol. 225 (C9), pp. 2206-2215.

Extended European Search Report for Application No. 15764795.9, dated Jul. 12, 2017, 9 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

COMMAND SHAPING TO DAMPEN VIBRATIONS IN MODE TRANSITIONS

CROSS-REFERENCE TO RELATED APPLICATIONS

The present application is a continuation of U.S. patent application Ser. No. 15/125,944 filed Sep. 13, 2016, which is the U.S. national phase of International Application No. PCT/US2015/020875, filed Mar. 17, 2015, which designated the U.S. and claims priority to U.S. Provisional Application No. 61/954,459 filed Mar. 17, 2014, entitled "COMMAND SHAPING TO DAMPEN VIBRATIONS IN USM MODE TRANSITIONS and U.S. Provisional Application No. 61/993,961, filed May 15, 2014, entitled "COMMAND SHAPING TO DAMPEN VIBRATIONS IN USM MODE TRANSITIONS", the entire contents of each of which are incorporated herein by reference.

BACKGROUND OF THE INVENTION

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three-dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system available from Intuitive Surgical, Inc. of Sunnyvale, Calif.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800,423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; the full disclosures of which are incorporated herein by reference.

A variety of structural arrangements can also be used to support and position the robotic surgical manipulator and the surgical instrument at the surgical site during robotic surgery. Supporting linkage mechanisms, sometimes referred to as set-up joints, or set-up joint arms, are often used to position and align each manipulator with the respective incision point in a patient's body. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, the full disclosures of which are incorporated herein by reference.

While the new telesurgical systems and devices have proven highly effective and advantageous, still further improvements are desirable. In general, improved minimally invasive robotic surgery systems are desirable. It would be particularly beneficial if these improved technologies enhanced the efficiency and ease of use of robotic surgical systems. For example, it would be particularly beneficial to increase maneuverability, improve space utilization in an operating room, provide a faster and easier set-up, inhibit collisions between robotic devices during use, and/or reduce the mechanical complexity and size of these new surgical systems.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

One embodiment of the present disclosure relates to a system for smooth mode transition during a robotic surgery. The system includes a patient side cart having a robotic mechanism that is moveable, and a processor that can control the robotic mechanism. The processor can determine a request for a mode transition, which request for mode transition can designate a new mode that is different than a current mode, determine initial parameters of the robotic mechanism, which initial parameters can include a position and a velocity of the robotic mechanism, calculate a smoothing curve that transitions between the current mode and the new mode and that can be C3 continuous, and move the robotic mechanism according to the smoothing curve.

In some embodiments of the system, the processor can identify degrees of freedom of the robotic mechanism affected by the mode transition. In some embodiments, the processor can calculate a smoothing curve for each of the identified degrees of freedom. In some embodiments, calculating the smoothing curve can include establishing a first command position, calculating a step value, and setting a second command position. In some embodiments, the second command position can be the first command position incremented by the calculated step value. In some embodiments the processor can determine if additional smoothing is desired, and establish a third command position and calculate a second step value if additional smoothing is desired. In some embodiments, the third command position can be set to the second command position.

In some embodiments, the initial parameters further include an acceleration parameter. In some embodiments, as a part of determining the request for the mode transition, the processor can determine if smoothing of the mode transition is indicated. In some embodiments, smoothing of the mode transition is indicated if estimated vibrations from the mode transition exceed a threshold value. In some embodiments, determining if smoothing of the mode transition is indicated includes determining post-mode-transition parameters of the robotic mechanism, wherein the post-mode-transition parameters include a position and a velocity of the robotic mechanism, determining the difference between the initial parameters and the post-mode-transition parameters, and comparing the difference between the initial parameters and the post-mode-transition parameters to a threshold. In some embodiments, smoothing of the mode transition is indicated if the difference between the initial parameters and the post-mode-transition parameters is greater than the threshold.

One embodiment of the present disclosure relates to a method for mode transition during a robotic surgery. The method can include determining a request for a mode transition, which request for mode transition can designate a new mode that is different than a current mode, determining initial parameters of a portion of a patient side cart, which initial parameters can include a position and a velocity, calculating a smoothing curve, which smoothing curve transitions between the current mode and the new mode, and which smoothing curve is C3 continuous, and moving the portion of the patient side cart according to the smoothing curve.

In some embodiments of the method, calculating the smoothing curve can include establishing a first command position, calculating a step value, and setting a second command position. In some embodiments, the second command position can include the first command position incremented by the calculated step value. In some embodiments, the method includes determining if additional smoothing is desired, and establishing a third command position and calculating a second step value if additional smoothing is desired. In some embodiments, the third command position is set to the second command position.

In some embodiments, the smoothing curve can include a plurality iteratively calculated steps. In some embodiments, the calculation of the smoothing curve is terminated when a second request for a mode transition is received. In some embodiments, the initial parameters can include an acceleration parameter.

One embodiment of the present disclosure relates to a method for vibration elimination during a robotic surgery. The method can include receiving a requested action, which requested action can include a change in a velocity or position of a portion of a patient side cart, calculating a smoothing curve, which smoothing curve can be calculated according to a simulated damping system. In some embodiments, the simulated damping system can include a first mass connected to a second mass via a first dashpot and a second dashpot connecting the first mass to ground. The method can include moving the portion of the patient side cart according to the smoothing curve.

In some embodiments of the method, the first and second masses have the same mass. In some embodiments, the first dashpot is defined by a first damping coefficient and the second dashpot is defined by a second damping coefficient. In some embodiments, the first and second damping coefficients are the same.

In some embodiments of the method, calculating the smoothing curve includes identifying an initial velocity of the portion of the patient side cart, a first initial velocity of the first mass, and a second initial velocity of the second mass. In some embodiments, the first and second initial velocities are set equal to the initial velocity of the portion of the patient side cart. In some embodiments, the method includes identifying a desired stopping point which identifies a location of the portion of the patient side cart when the requested action is received. In some embodiments, the portion of the patient side cart drifts beyond the desired stopping point when the portion of the patient side cart is moved according to the smoothing curve.

One embodiment of the present disclosure relates to a system for vibration elimination during a robotic surgery. The system includes a patient side cart that can include a movable manipulator, and a processor that can control the manipulator. In some embodiments, the processor can receive a requested action that requested action can include a change in a velocity or position of the manipulator, calculate a smoothing curve, which smoothing curve is calculated according to a simulated damping system corresponding to a first mass connected to a second mass via a first dashpot and a second dashpot connecting the first mass to ground, and move the manipulator according to the smoothing curve.

In some embodiments of the system, the first and second masses have the same mass. In some embodiments, the first dashpot is defined by a first damping coefficient and the second dashpot is defined by a second damping coefficient. In some embodiments, the first and second damping coefficients are the same.

In some embodiments of the system, calculating the smoothing curve includes identifying an initial velocity of the portion of the patient side cart, a first initial velocity of the first mass, and a second initial velocity of the second mass. In some embodiments, the first and second initial velocities are set equal to the initial velocity of the portion of the patient side cart.

In some embodiments, the processor can identify a desired stopping point which identifies a location of the portion of the patient side cart when the requested action is received. In some embodiments, the portion of the patient side cart drifts a distance beyond the desired stopping point when the portion of the patient side cart is moved according to the smoothing curve. In such an embodiment, the portion of the patient side cart does not return to the desired stopping point. In some embodiments, the portion of the patient side cart overshoots the desired stopping point when the portion of the patient side cart is not moved according to the smoothing curve. In such an embodiment, the overshoot arises due to oscillations of the portion of the patient side cart and the portion of the patient side cart returns to the desired stopping point. In some embodiments, a ratio of the drift distance to overshoot is at least 1.5:1.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1:
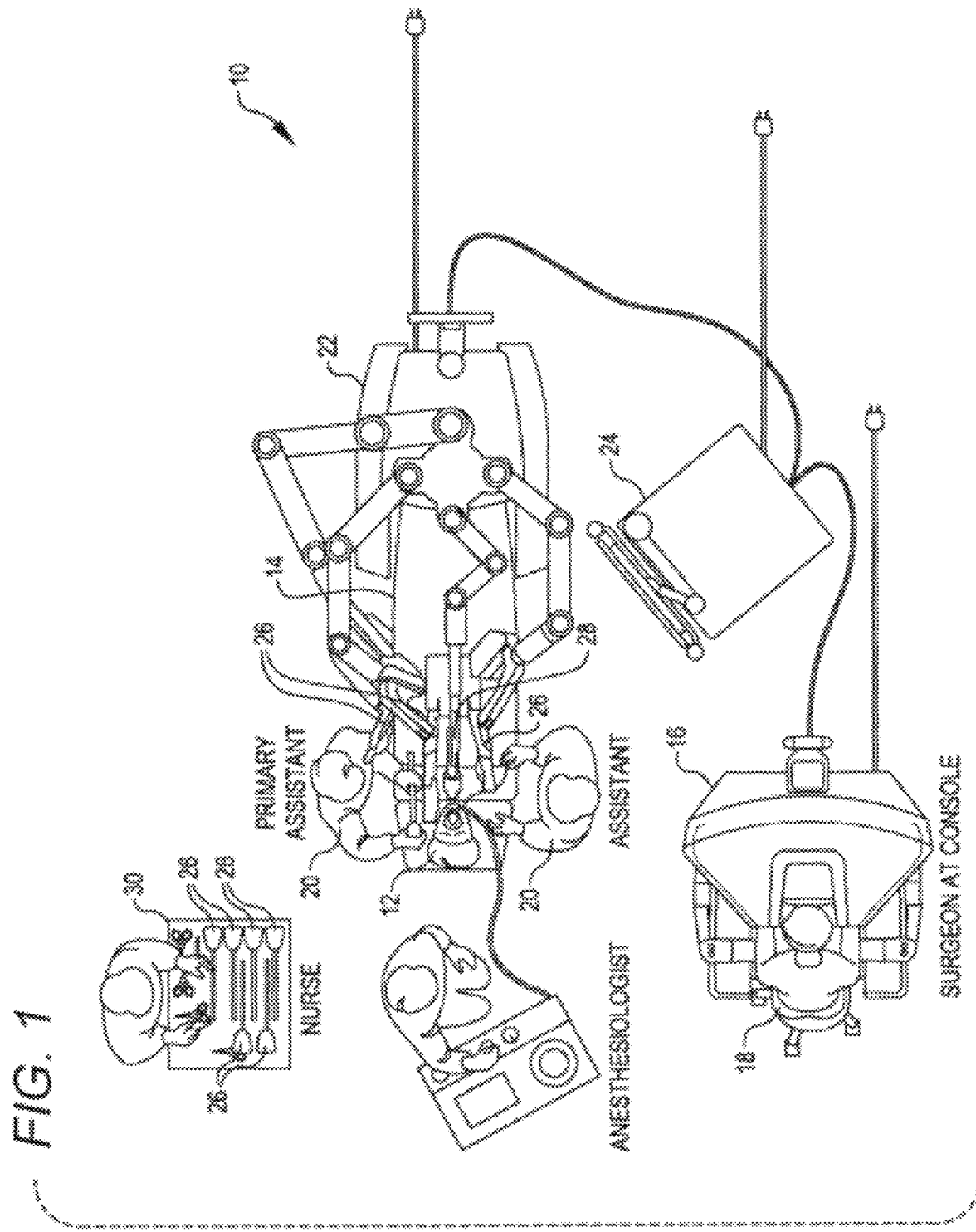
FIG. 1 is a plan view of a minimally invasive robotic surgery system being used to perform a surgery, in accordance with many embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The kinematic linkage structures and control systems described herein are particularly beneficial in helping system users to arrange the robotic structure of a procedure on a particular patient. Along with actively driven manipulators used to interact with tissues and the like during treatment, robotic surgical systems may have one or more kinematic linkage systems that are configured to support and help align the manipulator structure with the surgical work site. These set-up systems may be actively driven or may be passive, so that they are manually articulated and then locked into the desired configuration while the manipulator is used therapeutically. The passive set-up kinematic systems may have advantages in size, weight, complexity, and cost. Unfortunately, a plurality of manipulators may be used to treat tissues of each patient, the manipulators may each independently benefit from accurate positioning so as to allow the instrument supported by that instrument to have the desired motion throughout the workspace, and minor changes in the relative locations of adjacent manipulators may have significant impact on the interactions between manipulators (with poorly positioned manipulators potentially colliding or having their range and/or ease of motion significantly reduced). Hence, the challenges of quickly arranging the robotic system in preparation for surgery can be significant.

One option is to mount multiple manipulators to a single platform, with the manipulator-supporting platform sometimes being referred to as an orienting platform. The orienting platform can be supported by an actively driven support linkage (sometimes referred to herein as a set-up structure, and typically having a set-up structure linkage, etc.) The system may also provide and control motorized axes of the robotic set-up structure supporting the orienting platform with some kind of joystick or set of buttons that would allow the user to actively drive those axes as desired in an independent fashion. This approach, while useful in some situations, may suffer from some disadvantages. Firstly, users not sufficiently familiar with robotics, kinematics, range of motion limitations and manipulator-to-manipulator collisions may find it difficult to know where to position the orienting platform in order to achieve a good setup. Secondly, the presence of any passive joints within the system means that the positioning of the device involves a combination of manual adjustment (moving the passive degrees of freedom by hand) as well as controlling the active degrees of freedom, which can be a difficult and time-consuming iterative activity.

To maintain the advantages of both manual and actively-driven positioning of the robotic manipulators, embodiments of the robotic systems described herein may employ a set-up mode in which one or more joints are actively driven in response to manual articulation of one or more other joints of the kinematic chain. In many embodiments, the actively driven joints will move a platform-supporting linkage structure that supports multiple manipulators, greatly facilitating the arrangement of the overall system by moving those manipulators as a unit into an initial orientational and/or positional alignment with the workspace. Independent positioning of one, some, or all of the manipulators supported by the platform can optionally be provided through passive set-up joint systems supporting one, some, or all of the manipulators relative to the platform.

Minimally Invasive Robotic Surgery

Referring now to the drawings, in which like reference numerals represent like parts throughout the several views, FIG. 1 is a plan view illustration of a Minimally Invasive Robotic Surgical (MIRS) system 10, which can be, for example, a telesurgical system and/or a telepresence system, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
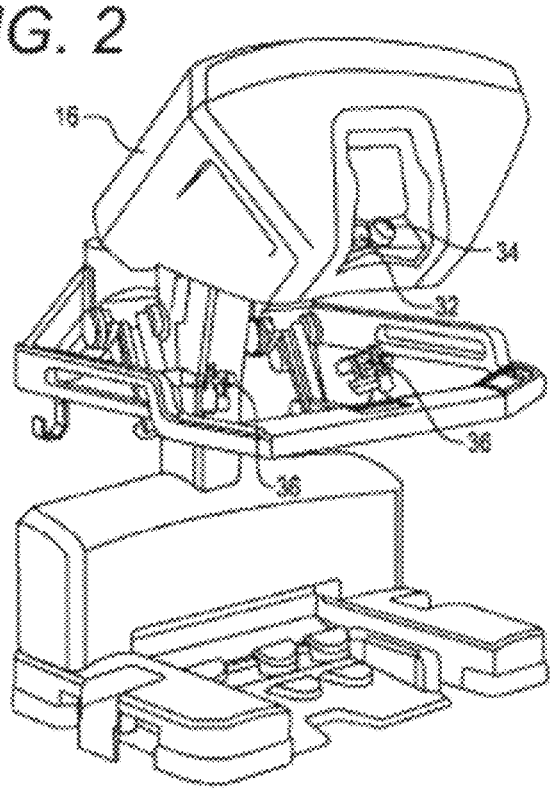
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
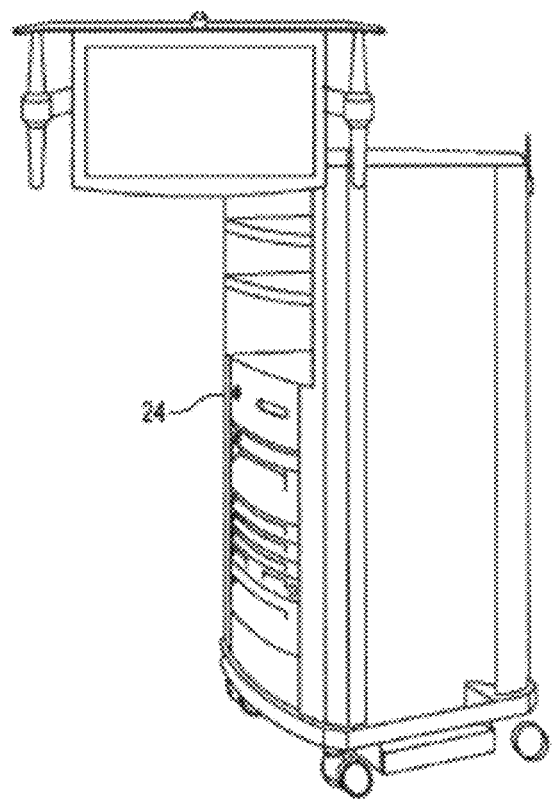
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
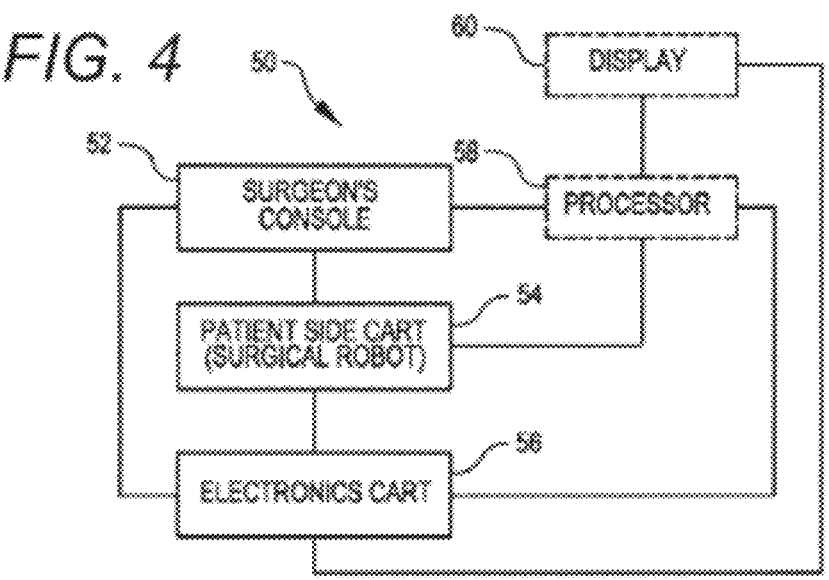
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Processor 58 will typically include a combination of hardware and software, with the software comprising tangible media embodying computer readable code instructions for performing the method steps of the control functionally described herein. The hardware typically includes one or more data processing boards, which may be co-located but will often have components distributed among the robotic structures described herein. The software will often comprise a non-volatile media and could also comprise a monolithic code but will more typically comprise a number of subroutines, optionally running in any of a wide variety of distributed data processing architectures.

Figure 5A:
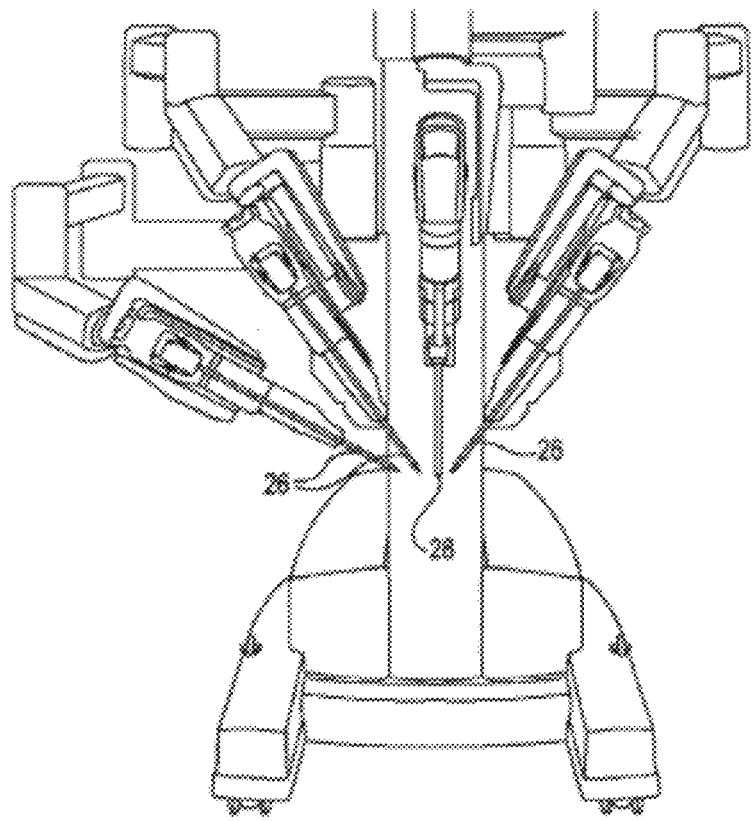
FIG. 5A is a partial view of a patient side cart (surgical robot) of a robotic surgery system, in accordance with many embodiments.
Figure 5B:
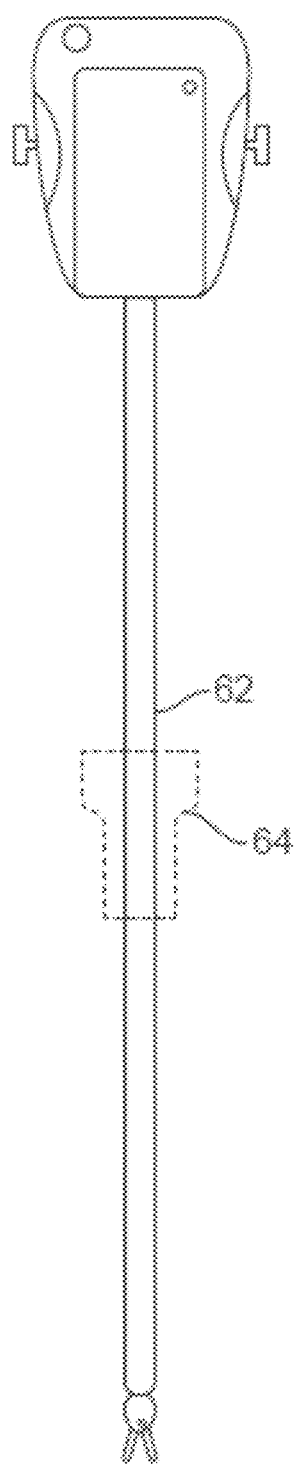
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Surgical tools 26 are inserted into the patient by inserting a tubular cannula 64 through a minimally invasive access aperture such as an incision, natural orifice, percutaneous penetration, or the like. Cannula 64 is mounted to the robotic manipulator arm and the shaft of surgical tool 26 passes through the lumen of the cannula. The manipulator arm may transmit signals indicating that the cannula has been mounted thereon.

Robotic Surgery Systems and Modular Manipulator Supports

Figure 6:
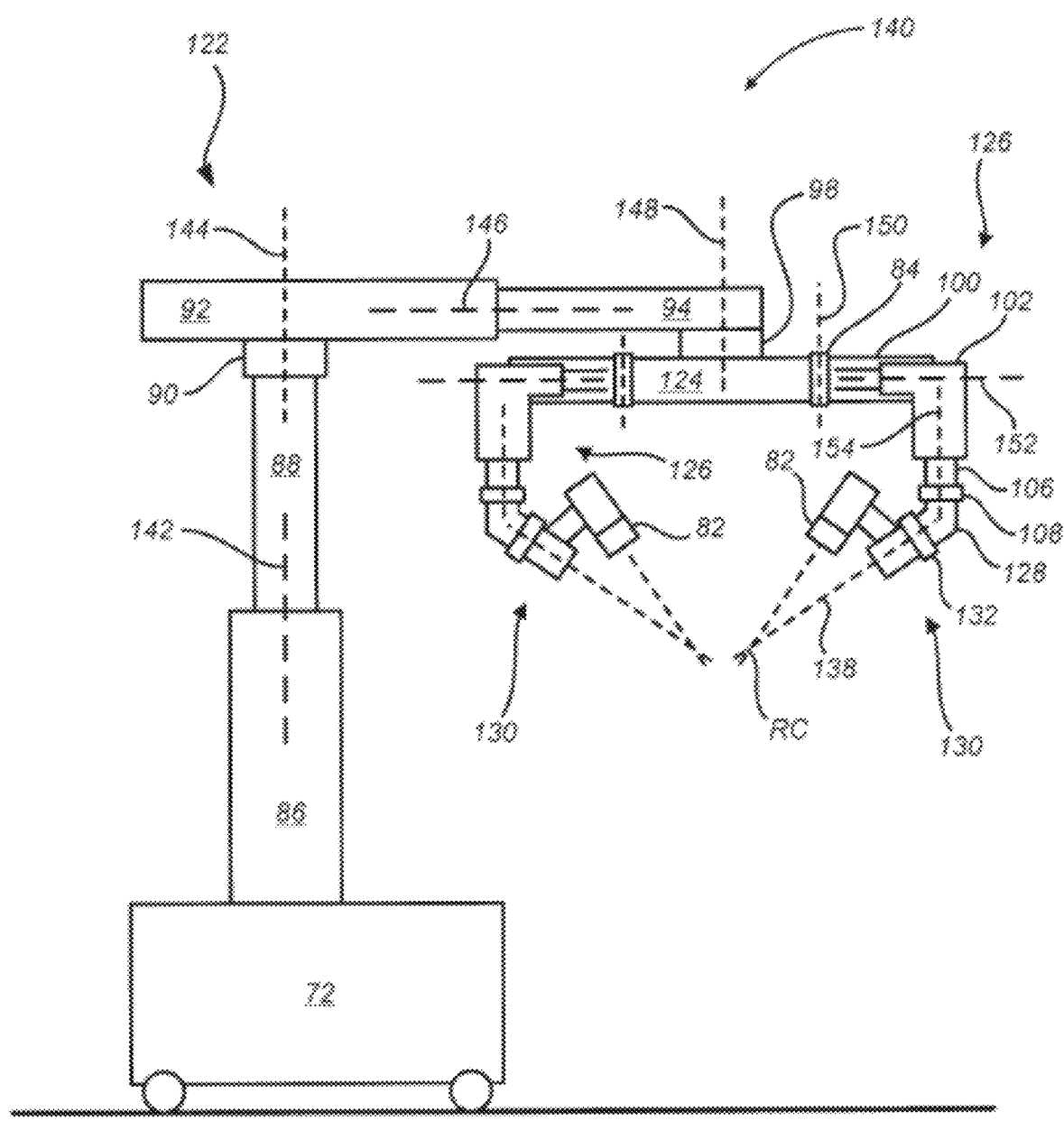
FIG. 6 shows a robotic surgery system, in accordance with many embodiments.

FIG. 6 is a simplified representation of a robotic surgery system 140, in accordance with many embodiments. The robotic surgery system 140 includes a mounting base 72, a support linkage 122, an orienting platform 124, a plurality of set-up linkages 126 (two shown), and a plurality of surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 126. Each of the set-up linkages 126 is rotationally coupled to and supported by the orienting platform 124 by a first set-up linkage joint 84. Each of the set-up linkages 126 is fixedly attached to and supported by the orienting platform 124. The orienting platform 124 is rotationally coupled to and supported by the support linkage 122. And the support linkage 122 is fixedly attached to and supported by the mounting base 72.

In many embodiments, the mounting base 72 is a movable and floor supported, thereby enabling selective repositioning of the overall surgery system 70, for example, within an operating room. The mounting base 72 can include a steerable wheel assembly and/or any other suitable support features that provide for both selective repositioning as well as selectively preventing movement of the mounting base 72 from a selected position. The mounting base 72 can also have other suitable configurations, for example, a ceiling mount, fixed floor/pedestal mount, a wall mount, or an interface configured for being supported by any other suitable mounting surface.

The support linkage 122 is configured to selectively position and orient the orienting platform 124 relative to the mounting base 72 via relative movement between links of the support linkage 122 along multiple set-up structure axes. The support linkage 122 includes a column base 86, a translatable column member 88, a shoulder joint 90, a boom base member 92, a boom first stage member 94, and a wrist joint 98. The column base 86 is fixedly attached to the mounting base 72. The translatable column member 88 is selectively repositionable relative to the column base 86 along a first set-up structure (SUS) axis 142, which is vertically oriented in many embodiments. In many embodiments, the translatable column member 88 translates relative to the column base 86 along a vertically oriented axis. The boom base member 92 is rotationally coupled to the translatable column member 88 by the shoulder joint 90. The shoulder joint 90 is operable to selectively orient the boom base member 92 relative to the translatable column member 88 around a second SUS axis 144, which is vertically oriented in many embodiments. The boom first stage member 94 is selectively repositionable relative to the boom base member 92 along a third SUS axis 146, which is horizontally oriented in many embodiments. Accordingly, the support linkage 122 is operable to selectively set the distance between the shoulder joint 90 and the distal end of the boom first stage member 94. And the wrist joint 98 is operable to selectively orient the orienting platform 124 relative to the boom first stage member 94 around a fourth SUS axis 148, which is vertically oriented in many embodiments.

Each of the set-up linkages 126 is configured to selectively position and orient the associated manipulator 82 relative to the orienting platform 124 via relative movement between links of the set-up linkage 126 along multiple set-up joint (SUJ) axes. Each of the first set-up linkage joint 84 is operable to selectively orient the associated set-up linkage base link 100 relative to the orienting platform 124 around a first SUJ axis 150, which in many embodiments is vertically oriented. Each of the set-up linkage extension links 102 can be selectively repositioned relative to the associated set-up linkage base link 10 along a second SUJ axis 152, which is horizontally oriented in many embodiments. Each of the set-up linkage vertical links 106 can be selectively repositioned relative to the associated set-up linkage extension link 102 along a third SUJ axis 154, which is vertically oriented in many embodiments. Each of the second set-up linkage joints 108 is operable to selectively orient the mechanism support link 128 relative to the set-up linkage vertical link 106 around the third SUJ axis 154. Each of the joints 132 is operable to rotate the associated manipulator 82 around the associated axis 138.

Figure 7:
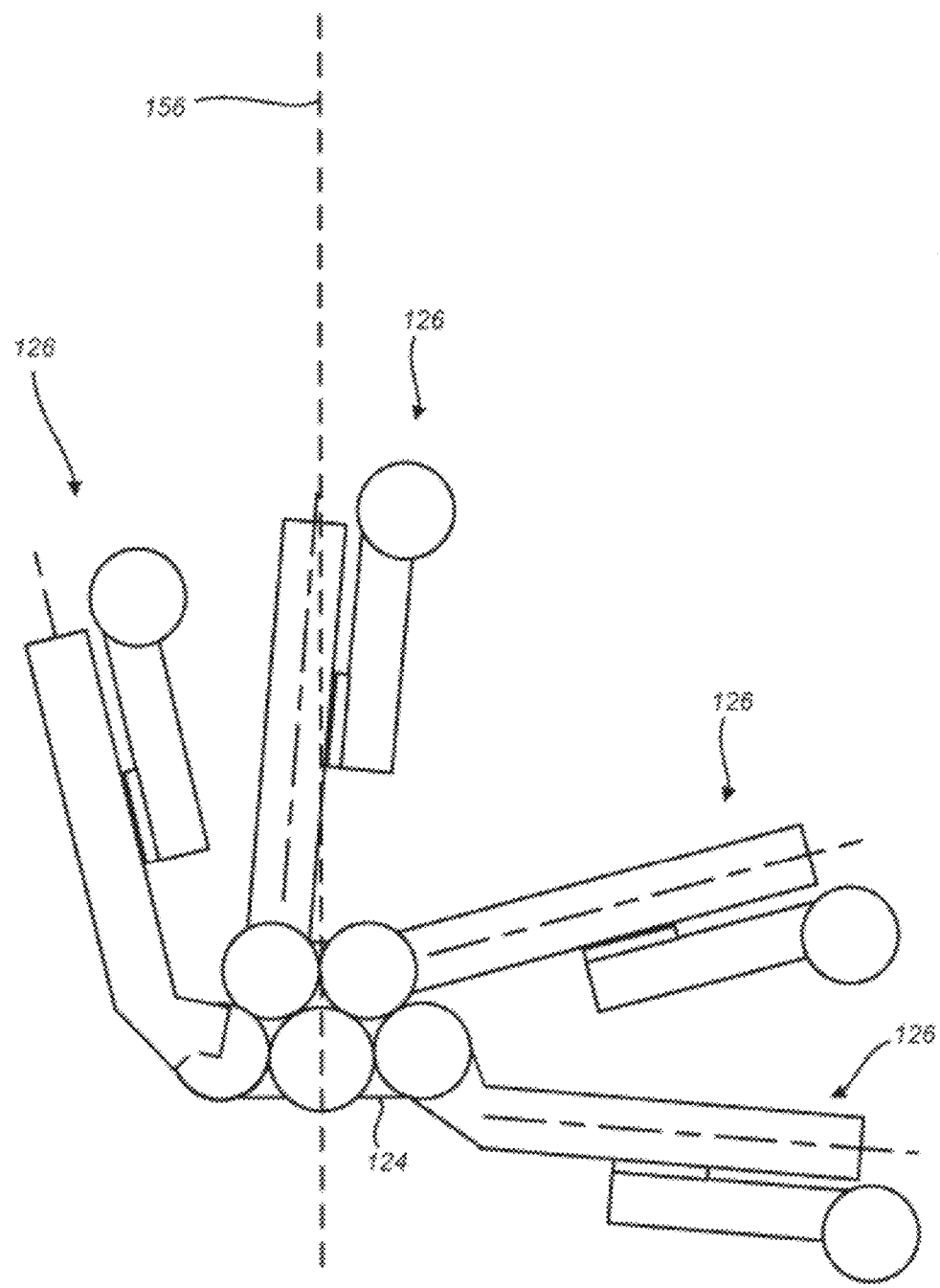
FIG. 7 illustrates rotational orientation limits of set-up linkages relative to an orienting platform of the robotic surgery system of FIG. 6.

FIG. 7 illustrates rotational orientation limits of the set-up linkages 126 relative to the orienting platform 124, in accordance with many embodiments. Each of the set-up linkages 126 is shown in a clockwise limit orientation relative to the orienting platform 124. A corresponding counter-clockwise limit orientation is represented by a mirror image of FIG. 7 relative to a vertically-oriented mirror plane. As illustrated, each of the two inner set-up linkages 126 can be oriented from 5 degrees from a vertical reference 156 in one direction to 75 degrees from the vertical reference 156 in the opposite direction. And as illustrated, each of the two outer set-up linkages can be oriented from 15 degrees to 95 degrees from the vertical reference 156 in a corresponding direction.

Figure 8:
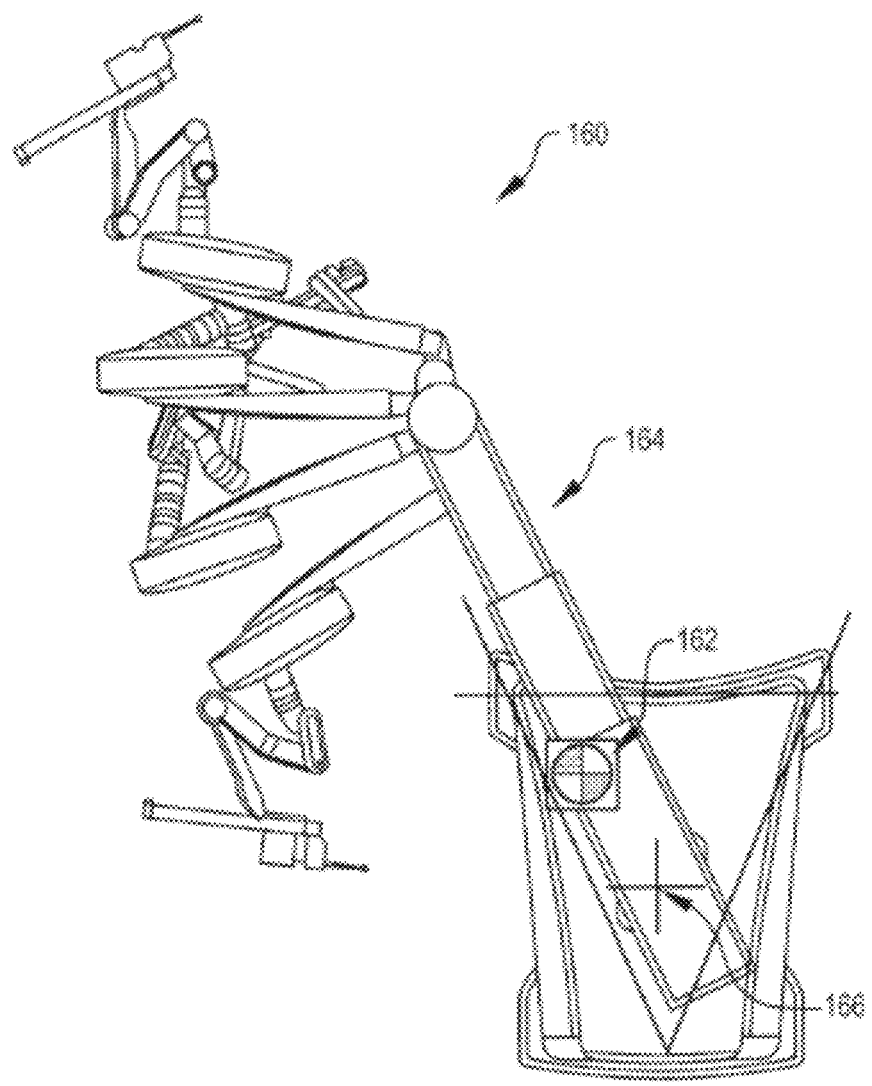
FIG. 8 shows a center of gravity diagram associated with a rotational limit of the boom assembly for a robotic surgery system, in accordance with many embodiments.

FIG. 8 shows a center of gravity diagram associated with a rotational limit of a support linkage for a robotic surgery system 160, in accordance with many embodiments. With components of the robotic surgery system 160 positioned and oriented to shift the center-of-gravity 162 of the robotic surgery system 160 to a maximum extent to one side relative to a support linkage 164 of the surgery system 160, a shoulder joint of the support linkage 164 can be configured to limit rotation of the support structure 164 around a set-up structure (SUS) shoulder-joint axis 166 to prevent exceeding a predetermined stability limit of the mounting base.

Figure 9:
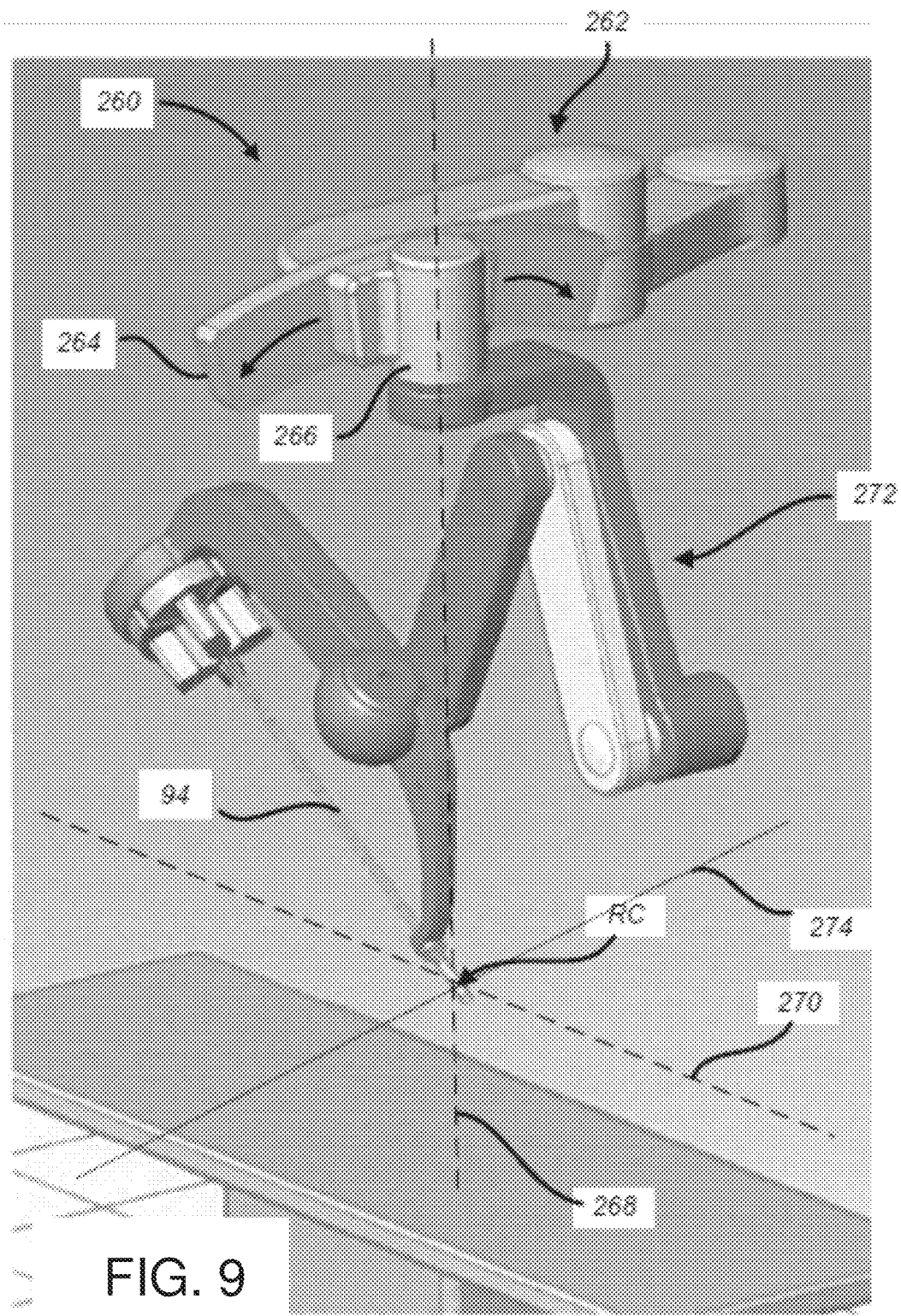
FIG. 9 shows a remote center manipulator, in accordance with many embodiments, that includes a curved feature having a constant radius of curvature relative to the remote center of manipulation and along which a base link of the outboard linkage can be repositioned.

FIG. 9 illustrates another approach for the implementation of a redundant axis that passes through the remote center of manipulation (RC) and the associated redundant mechanical degree of freedom. FIG. 9 shows a remote center manipulator 260, in accordance with many embodiments, that includes a mounting base 262 that includes a curved feature 264 having a constant radius of curvature relative to the remote center of manipulation (RC) and along which a base link 266 of the outboard (proximal) linkage of the manipulator 260 can be repositioned. The outboard linkage is mounted to the base link 266, which includes a "yaw" joint feature, for rotation about a first axis 268 that intersects the remote center of manipulation (RC). The base link 266 is interfaced with the curved feature 264 such that the base link 266 is constrained to be selectively repositioned along the curved feature 264, thereby maintaining the position of the remote center of manipulation (RC) relative to the mounting base 262, which is held in a fixed position relative to the patient. The curved feature 264 is configured such that movement of the base link 266 is limited to rotation about a second axis 270 that intersects the remote center of manipulation (RC). By changing the position of the base link 266 along the curved feature 264, the orientation of the outboard linkage of the manipulator 260 relative to the patient can be varied, thereby providing for increased range of motion of the surgical instrument manipulated by the remote center manipulator 260. Parallelogram mechanism 272 provides rotation around axis 274. It can be seen that as the entire parallelogram mechanism rotates around axis 268, axes 270 and 274 can be made coincident.

Figure 10:
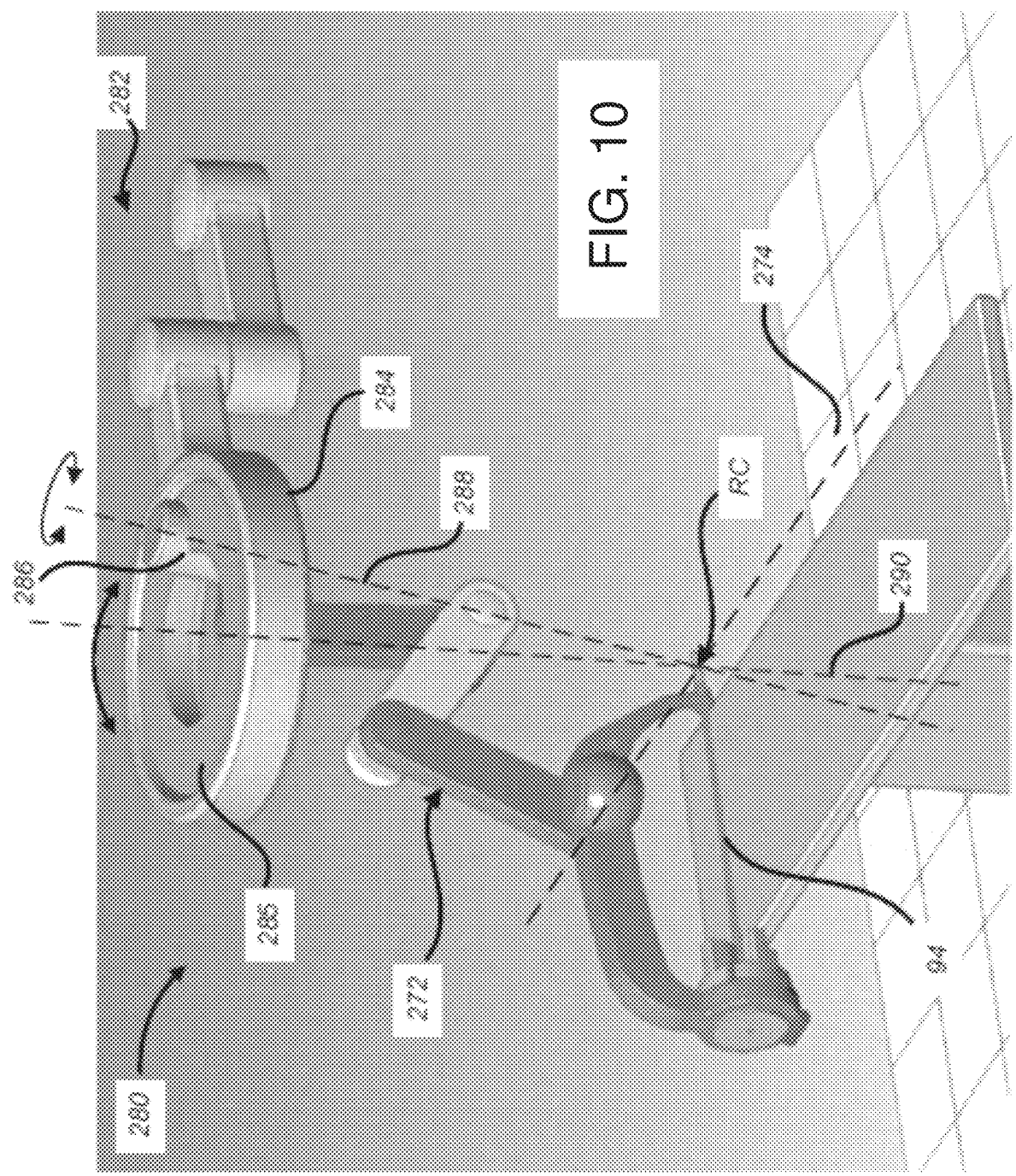
FIG. 10 shows a remote center manipulator, in accordance with many embodiments, that includes a closed-loop curved feature to which a base link of the outboard linkage is interfaced such that the base link is constrained to move along the closed-loop curved feature.

FIG. 10 illustrates another approach for the implementation of a redundant axis that passes through the remote center of manipulation (RC), providing an associated redundant degree of freedom. FIG. 10 shows a remote center manipulator 280, in accordance with many embodiments, that includes a mounting base 282 that includes a closed-loop curved feature 284 inside which a base link 286 of the outboard (distal) linkage of the manipulator 280 can be repositioned. As shown, central mount element 285 rotates inside closed-loop curved feature 284. Base link 286 is mounted on the central mount element 285 to be oriented somewhat inward toward the remote center of manipulation. The outboard linkage is mounted to the base link 286 for rotation about a first axis 288 that intersects the remote center of manipulation (RC). The closed-loop curved feature 284 is configured such that, for all positions of the base link 286 around the curved feature 284, the position of the remote center of manipulation (RC) remains fixed relative to the mounting base 282, which is held fixed relative to the patient. The closed-loop curved feature 284 is circular and is axially-symmetric about a second axis 290 that intersects the remote center of manipulation (RC). By changing the position of the base link 286 around the closed-loop curved feature 284, the orientation of the outboard linkage of the manipulator 280 relative to the patient can be varied, thereby providing for increased range of motion, arm-to-arm or arm-to-environment collision avoidance, and/or kinematic singularity avoidance for the remote center manipulator 280. A "partial circle" feature or a full circular feature where the mounting base only traverses a portion of the circle can also be used. It can be seen that curved feature 284 and its associated central mount feature 285 act as a conical sweep joint.

Figure 11:
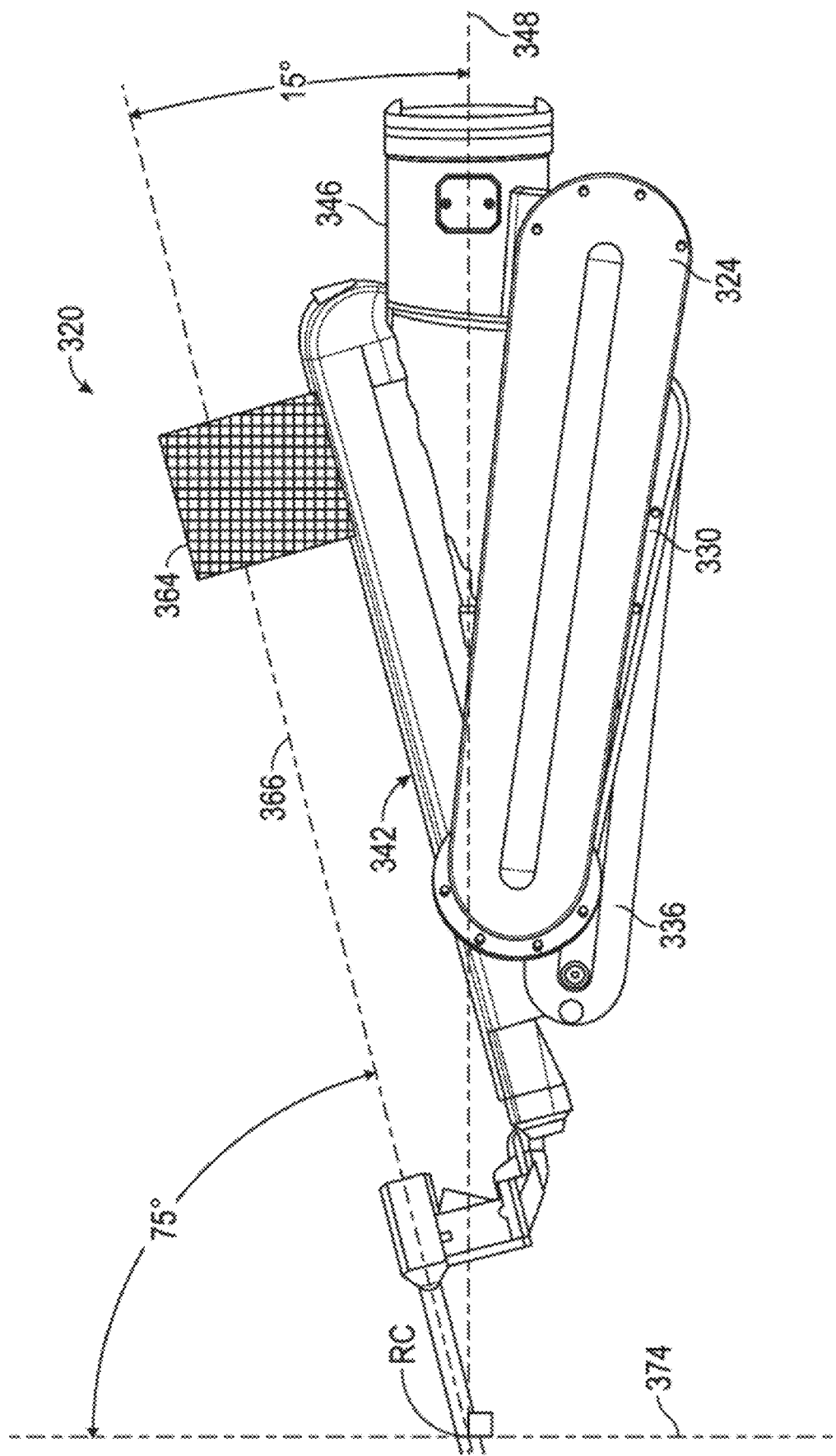
FIG. 11 is a side view of the remote center manipulator in a configuration of maximum pitch back of the instrument holder relative to the remote center of manipulation, in accordance with many embodiments.

FIG. 11 is a side view of the remote center manipulator 320 in which the instrument holder 342 is pitched back to a maximum amount. In the configuration shown, the first parallelogram link 330 has been swung to a position just past being aligned with the extension link 324 and the second parallelogram link 336 has been swung to a position just past being aligned with the first parallelogram link 330, thereby orienting the insertion axis 366 to an angular offset of 75 degrees from a perpendicular 374 to the yaw axis 348. While the remote center manipulator 320 can be configured to achieve even greater maximum pitch back angle, for example, by increasing the length of the extension link 324 such that the instrument holder 342 does not come into contact with the yaw/pitch housing 346, the additional pitch back angle gained may not be of practical value given that the kinematics of the remote center manipulator 320 with regard to yawing of the instrument holder 342 relative to the remote center of manipulation (RC) becomes increasingly poorly conditioned when the angle between the insertion axis 366 and the yaw axis 348 is reduced below 15 degrees.

Command Shaping

Figure 12:
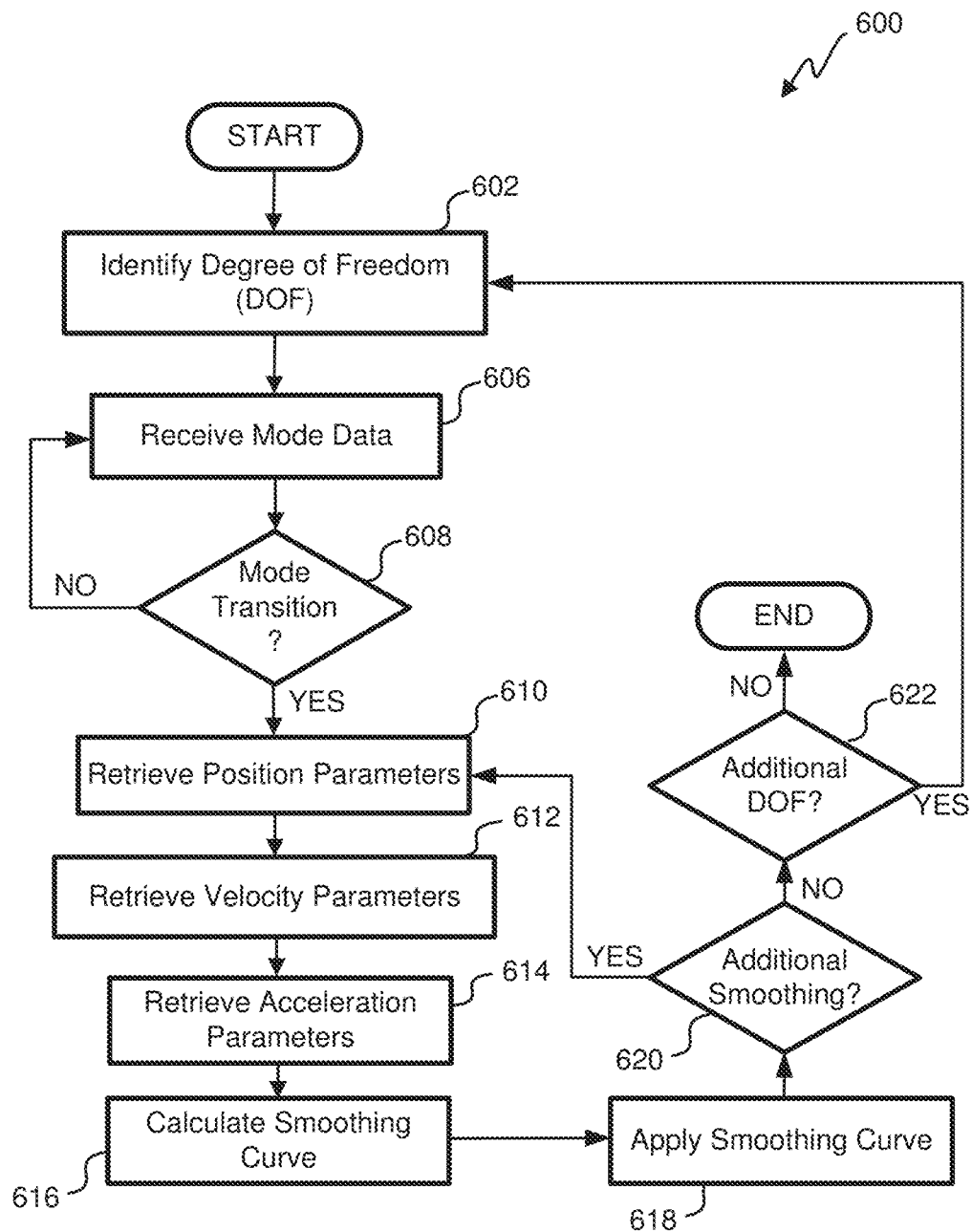
FIG. 12 is a flowchart illustrating one embodiment of a process for command shaping to dampen vibrations.

FIG. 12 is a flowchart illustrating one embodiment of a process 600 for command shaping to dampen vibrations. The process 600 can be used to smooth movements of a robotic system, such as the MIRS system 10, and specifically of the Patient Side Cart 22. In some embodiments, the process 600 can be performed when the robotic system, such as the MIRS system 10 changes modes, and in some embodiments, the process 600 can be performed regardless of any mode change by the robotic system. The process 600 can be performed using a processor and/or control system that is part of the robotic system and/or connected to the robotic system. In some embodiments, the process 600 can be performed by, for example, the processor 58.

The process 600 begin at block 602 wherein a degree of freedom (DOF) is identified. In some embodiments, the degree of freedom, can be one of the degrees of freedom (DOFs) of the MIRS system 10 and/or of a component, joint, or feature of the MIRS system 10. In some embodiments, the identified degrees of freedom can relate to portions of the MIRS system 10 that are affected by the mode change. In some embodiments, information relating to these degrees of freedom can be stored in memory associated with the MRS system 10, which memory can be, for example, connected with the processor 58. In some embodiments, information relating to the one or several of the degrees of freedom can be retrieved from the memory, and/or generated or collected.

After the degree of freedom has been identified in block 602, the process 600 proceeds to block 606 wherein mode data is received. In some embodiment the mode data can identify one or several modes of operation of the MIRS system 10. In one embodiment, for example, this mode data can identify the current mode of operation of the MIRS system 10, one or several past modes of operation of the MIRS system 10, and/or a future or requested mode of operation of the MRS system 10. In some embodiments, the identification of a requested mode of operation that is different from the current mode of operation can result in a mode transition, which can, in some embodiments, and without the herein disclosed command shaping, generate significant vibrations. In some embodiments, the mode data can be received from the memory, the Surgeon's Console 16, and/or the Electronics Cart 24.

After the mode data has been received, the process 600 proceeds to decision state 608, wherein it is determined if a mode transition has occurred and/or is occurring. The determination of whether a mode transition has occurred and/or is occurring can include comparing information relating to the operation of the MIRS system 10 with criteria for determining whether a mode transition has occurred and/or is occurring. In some embodiments, these criteria can include determining whether any action, whether associated with a mode transition or not, has been requested that will and/or is likely to generate vibrations and/or whether these vibrations are greater than, less than, or equal to some threshold value. In some embodiments, a requested action will and/or is likely to generate vibrations when the requested action is achieved through accelerations of one or several components of the MIRS system 10 that are greater than the threshold value. In some embodiments, the threshold value can vary based on a number of factors including, for example, the source of the force giving rise to the accelerations, the degree of rigidity of the portion of the MIRS system 10 experiencing the forces and/or accelerations, and/or the like. In some embodiments, this determination can further include determining whether the requested action, including, for example, a requested mode transition will translate a portion of the MIRS system 10 from being static to being dynamic, or from being dynamic to being static. This determination can be made by the processor 58 and/or other component of the MIRS system 10.

In some embodiments, the determination of whether a mode transition has occurred can further include determining whether smoothing and/or command shaping has been requested. In some embodiments this determination can be made based on one or several inputs received from the surgeon and/or other user of the MIRS system 10. In one embodiment, this information can be stored within the memory, and can be retrieved when the process 600 is performed by, for example, the processor 58.

After it has been determined whether a mode transition has occurred and/or is occurring, the process 600 proceeds to block 610 wherein position parameters are retrieved. In some embodiments, the position parameters can define and/or identify the position of one or several components of the MIRS system 10. In some embodiments, the position parameters can define and/or identify the position of one or several components of the MIRS system 10 absolutely, such as, for example, with respect to a fixed coordinate system, and/or relatively with respect to one or several other components of the MIRS system 10. In some embodiments, the position parameters can be retrieved from and/or determined by the MIRS system 10.

After the position parameters have been retrieved, the process 600 proceeds to block 612, wherein velocity parameters are retrieved. In some embodiments, the velocity parameters can define and/or identify the velocity of one or several components of the MIRS system 10. In some embodiments, the velocity parameters can define and/or identify the velocity of one or several components of the MIRS system 10 absolutely, such as, for example, with respect to a fixed coordinate system, and/or relatively with respect to one or several other components of the MIRS system 10. In some embodiments, the velocity parameters can be retrieved from and/or determined by the MIRS system 10.

After the velocity parameters have been retrieved, the process 600 proceeds to block 614, wherein acceleration parameters are retrieved. In some embodiments, the acceleration parameters can define and/or identify the acceleration of one or several components of the MIRS system 10. In some embodiments, the acceleration parameters can define and/or identify the acceleration of one or several components of the MIRS system 10 absolutely, such as, for example, with respect to a fixed coordinate system, and/or relatively with respect to one or several other components of the MIRS system 10. In some embodiments, the acceleration parameters can be retrieved from and/or determined by the MIRS system 10.

After the acceleration parameters have been retrieved, the process 600 proceeds to block 616 wherein a smoothing curve is calculated. The smoothing curve can be made of a plurality of steps that are iteratively calculated. In some embodiments, the smoothing curve can define a transitional path between the current location, velocity, and/or acceleration of the MIRS system 10 and/or component thereof, and the location, velocity and/or acceleration specified by the requested action and/or mode transition. In some embodiments, the transitional path can be a path that minimizes and/or eliminates vibration. In one embodiment, the transitional path can be free from discontinuities such as, a discontinuity in the position, velocity, acceleration, jerk, and/or other parameter of the MIRS system 10 and/or component thereof affected by the requested action and/or mode transition. In one embodiment, a transitional path that has no discontinuities in velocity is C1 continuous, a transitional path that has no discontinuities in acceleration is C2 continuous, and a transitional path that has no discontinuities in jerk is C3 continuous. In some embodiments, the calculation of the smoothing curve can include calculating one or several next positions, velocities, accelerations, jerks, and/or other parameter for the MIRS system 10 and/or component thereof. In some embodiments, these one or several next positions, velocities, accelerations, jerks and/or other parameters of the MIRS system 10 and/or component thereof can be calculated indefinitely, until a triggering threshold has been achieved, and/or until another action has been requested that triggers re-initiation of the process 600. The smoothing curve can be calculated by the processor 58 or other component of the MIRS system 10. The details of the calculation of the smoothing curve will be discussed at greater length below.

After the smoothing curve has been calculated, the process 600 proceeds to block 618, wherein the smoothing curve is applied. As discussed above, in some embodiments, the smoothing curve can comprise one or several next positions, velocities, accelerations, jerks, and/or other parameter for the MIRS system 10 and/or component thereof. In some embodiments, the smoothing curve can be applied to the MIRS system 10 and/or component thereof including, for example, one or several motors that manipulate the MIRS system 10 and/or components thereof. The application of the smoothing curve can be controlled by the processor 58 or other component of the MIRS system 10.

After the soothing curve has been applied, the process 600 proceeds to decision state 620 wherein it is determined if additional smoothing is required and/or desired. In some embodiments, this can include determining whether to terminate the smoothing process by, for example, comparing one or several parameters of the MIRS system 10 and/or component thereof with the threshold identifying when smoothing can and/or should be terminated. In some embodiments, the determination of whether to provide additional smoothing can comprise determining whether an additional action has been requested which can include, for example, an additional mode transition. This determination can be made, for example, by the processor 58. If it is determined that additional smoothing is required, then the process 600 returns to block 610 and proceeds as outlined above.

Process 600 can include parallel/simultaneous processing or sequential processing for degrees of freedom of the MRS system 10. In some embodiments in which the degrees of freedom are parallel/simultaneously processed, decision state 622 as depicted in FIG. 12 may be omitted. Returning again to process 600, if it is determined that no additional smoothing is required, then the process proceeds to decision state 622 wherein it is determined if there are any additional degrees of freedom associated with the MIRS system 10. If it is determined that there is an additional, as yet unidentified degree of freedom, the process 600 returns to block 602 and proceeds as outlined above. If it is determined that there are no additional and/or identified degrees of freedom associated with the MIRS system 10, then the process can, in some embodiments, terminate.

Figure 13:
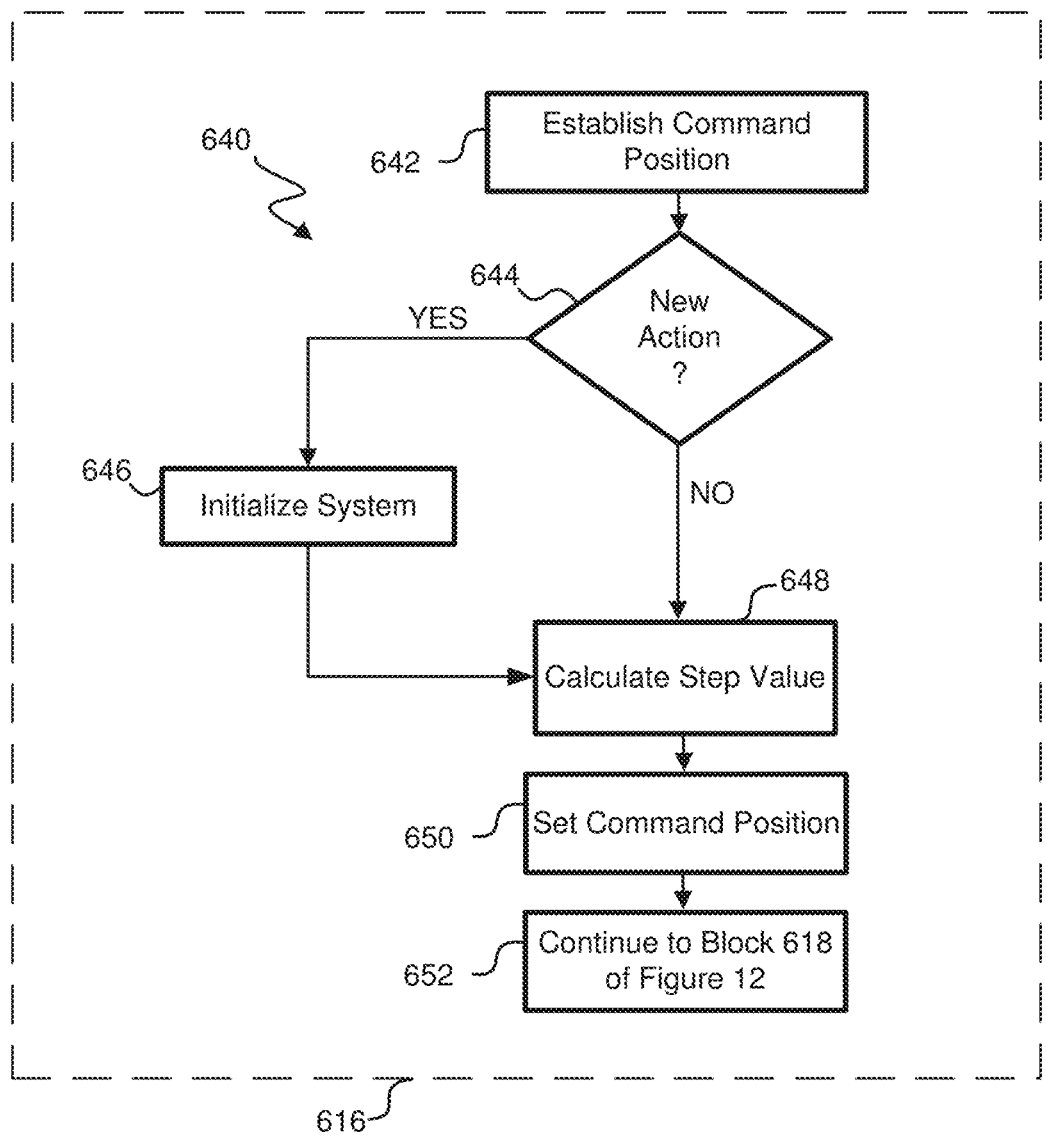
FIG. 13 is a flowchart illustrating one embodiment of a process for calculating a smoothing curve.

FIG. 13 is a flowchart illustrating one embodiment of a process 640 for calculating the smoothing curve is shown. In some embodiments, the process 640 can be performed in the place of block 616 shown in FIG. 12. Like the process 600 of FIG. 12, the process 640 can be performed by the MIRS system 10 and/or components thereof.

The process 640 begins at block 642 wherein a command position is established. In some embodiments, the command position can be the current position of the MRS system 10 and/or component thereof subject to the requested action. After the command position has been established, the process 640 proceeds to decision state 644 wherein it is determined if the requested action is a new action. In some embodiments, this determination can include determining whether smoothing has already occurred for the requested action and/or has already been initiated for the requested action. If the smoothing has already occurred and/or has already been initiated, then the process 640 proceeds to block 646 wherein the system is initialized. In some embodiments, the initialization the system can include establishing one or several initial parameters for generation of the smoothing curve. In some embodiments, this can include establishing parameters specifying one or several damping coefficients, locations, velocities, or the like.

After the system has been initialized, the process 640 proceeds to block 648 wherein a step value is calculated. In some embodiments, the step value can be a value defining one or several next parameters of location and the/or velocity of a simulated damping system, the MIRS system 10 and/or components thereof that are affected by the requested action. The details of such a simulated damping system will be discussed at further length below.

In some embodiments, the step value can be calculated such that the MIRS system 10 and/or components thereof experience no jerk when moving from the command position to the position specified by the step value in the manner specified by the step value. The step value can be calculated using the processor 58. Details of how the step value can be calculated will be discussed at greater length below.

After the step value has been calculated, the process 640 proceeds to block 650 wherein a new command position is set. In some embodiments, the new command position can be set to the calculated step value, one of the calculated step values, or a combination of the initially established command position and the calculated step value. The command position can be stored in memory associated with the MIRS system 10. After the command position has been set, the process 640 proceeds to block 652 and continues to block 618 of FIG. 12.

Figure 14A:
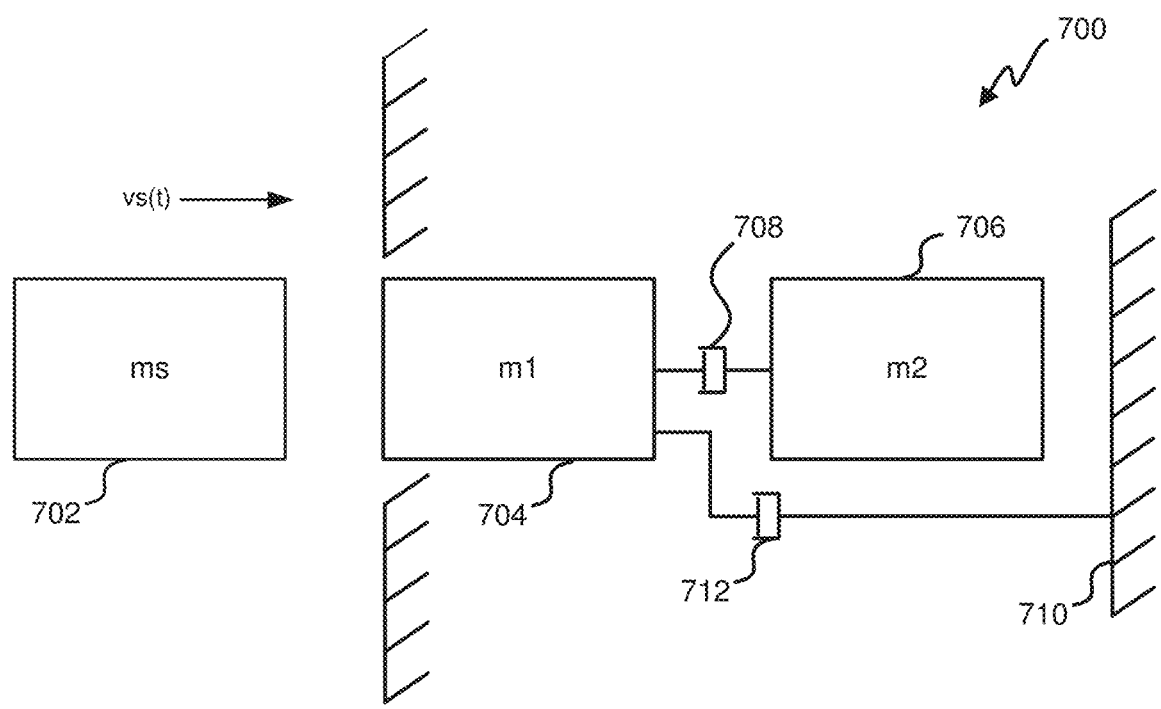
FIGS. 14A and 14B are graphical illustrations of one embodiment of a mechanical system used for calculating a smoothing curve.
Figure 14B:
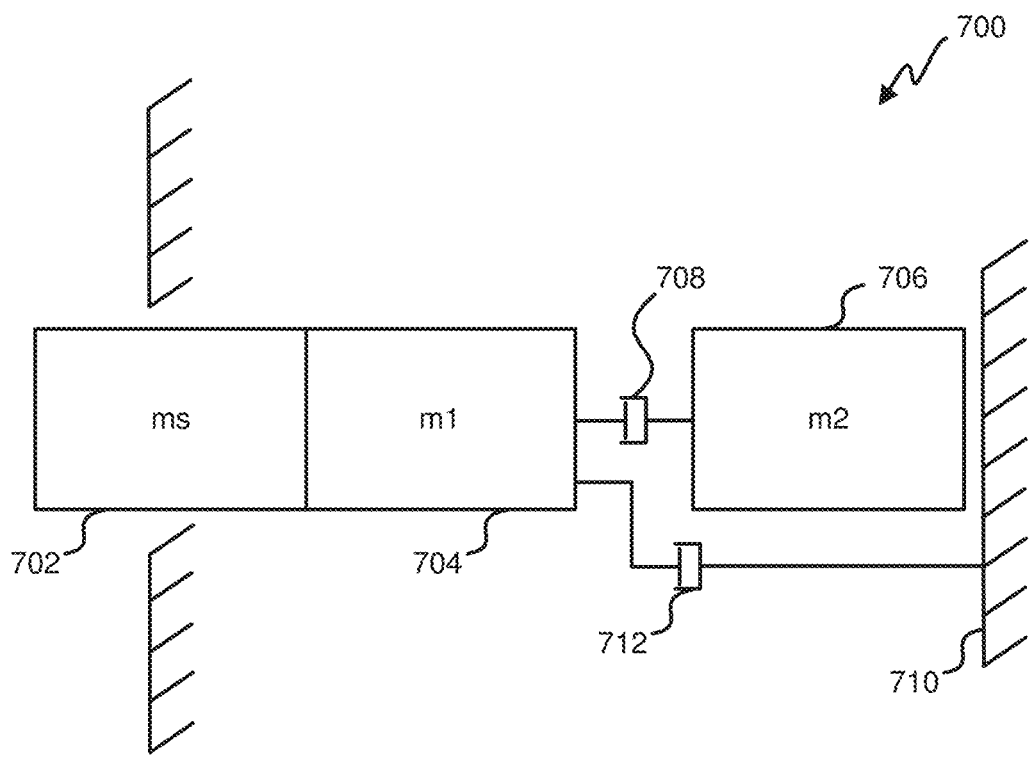

FIGS. 14A and 14B are graphical illustrations of one embodiment of a mechanical system and/or a simulated damping system 700 used for calculating a smoothing curve. In FIG. 14A, the simulated damping system 700 is depicted as having a moving part, and in FIG. 14B, the simulated damping system 700 is depicted after all of the movement has been stopped and/or effectively stopped. The same simulated damping system 700 can be used to determine a smoothing curve to stop motion and/or to slow motion, and in some embodiments, the simulated damping system 700 can be used to determine a smoothing curve to start and/or accelerate motion.

The simulated damping system 700 includes a system mass 702. The system mass 702 represents the mass of the MIRS system 10 and the/or the component of the MIRS system 10 that is affected by the requested action. The value of the system mass 702 can be stored in memory associated with the MIRS system 10, and/or can be generated based on feedback received from components of the MIRS system 10 such as, for example, one or several motors. In some embodiments, the system mass can be determined based on the amount of force needed to achieve a desired acceleration. As depicted in FIGS. 14A and 14B, the system mass has a velocity indicated as vs(t), which varies over time as a function of the interaction of the system mass 702 with other components of the simulated damping system 700. The simulated damping system 700 includes a first mass 704 that interacts with a second mass 706 via a first dashpot 708, and with ground 710 via a second dashpot 712. In some embodiments, the first and second masses 704, 706 can have any desired value identifying the masses of the first and second mass 704, 706. In some embodiments, the mass of the first mass 704 can be the same as the mass of the second mass, and in some embodiments, the mass of the first mass 704 can be different than the mass of the second mass 706. In some embodiments, the masses of the first and second mass 704, 706 can be selected so, in combination with the first and second dashpots 708, 712, the simulated damping system 700 can create a C1, C2, C3, C4, C5, and/or a C6 continuous smoothing curve for the parameters of the system mass 702. In some embodiments, a variety of masses of the first and second mass 704, 706 can result in the creation of a C1, C2, C3, C4, C5, and/or a C6 continuous smoothing curve for the parameters of the system mass 702.

Similarly, the first dashpot 708 and the second dashpot 712 can each be described by, for example, a damping coefficient. In some embodiments, the damping coefficients of the first dashpot 708 can be the same as the damping coefficient of the second dashpot 712, and in some embodiments, the damping coefficient of the first dashpot 708 can be different than the damping coefficient of the second dashpot 712.

In some embodiments, the damping coefficients of the dashpots 708, 712 can be configured to mitigate and the/or eliminate total travel distance experienced by the MIRS system 10 and/or a component of the MIRS system 10 affected by the requested action between the time when the action is requested and the time when the MIRS system 10 and/or component of the MIRS system 10 affected by the requested action completes the requested action and the/or effectively completes the requested action. In some embodiments, the requested action is effectively completed when the MIRS system 10 and/or component of the MIRS system 10 affected by the requested action asymptotically approaches the position, velocity, and/or acceleration specified in the requested action.

In some embodiments, the damping coefficients of the dashpots 708, 712 can be configured so as to mitigate and/or eliminate vibrations arising by the execution of the requested action. In some embodiments the values of the damping coefficients of the dashpot's 708, 712 can be optimized so as to provide the outcome that least affects the ability of the surgeon to control the MIRS system 10 and/or that least adversely affects the outcome of the operation performed by the MIRS system 10. In some embodiment a specific mass and/or specific masses of the first and second mass 704, 706, as well as the damping coefficients of the first and second dashpots 708, 712 can be simultaneously selected to optimize desired performance and/or response of simulated damping system 700 and/or the shape and/or trajectory of the smoothing curve.

Figure 15:
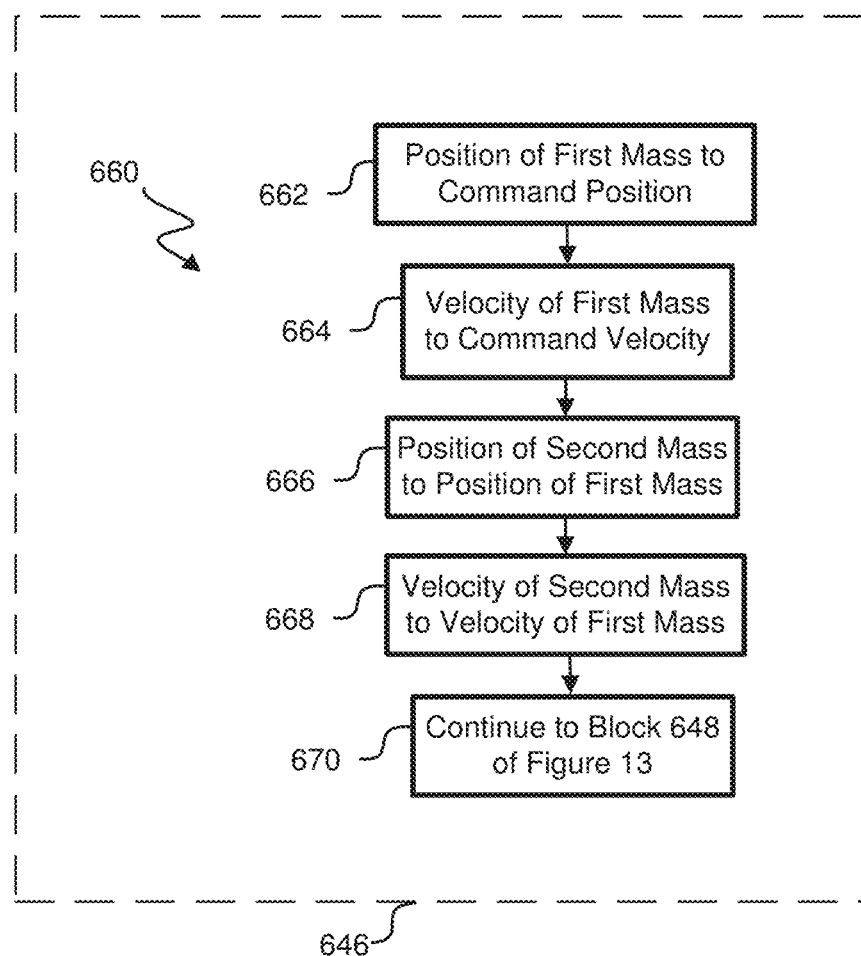
FIG. 15 is a flowchart illustrating one embodiment of a process for initializing a command shaping algorithm.

FIG. 15 is a flowchart illustrating one embodiment of a process 660 for initializing a command shaping algorithm. The process 660 can be performed as part of, or in the place of block 646 of FIG. 13. The process begins at block 662 wherein the position of the first mass is designated as equal to the command position established in block 642 of FIG. 13. After the position the first mass 704 is set as equal to the command position, the process 660 proceeds to block 664 when the velocity of the first mass 704 is set equal to the command velocity, in other words equal to velocity vs(t) of the system mass 702 immediately before the action is requested.

After the velocity the first mass 704 is set equal to the command velocity, the process 660 proceeds to block 666 wherein the position of the second mass 706 is set equal to the position of the first mass 704, and thus set as equal to the command position established in block 642 of FIG. 13. After the position the second mass 706 is set as equal to the command position, the process 660 proceeds to block 668 wherein the velocity of the second mass 706 is set equal to the velocity of the first mass 704, or in other words is set equal to the command velocity, which is velocity vs(t) of the system mass 702 immediately before the action is requested. After the velocity of the second mass 706 has been set to the velocity of the first mass 704, the process 660 proceeds to block 670 and continues to block 648 of FIG. 13.

Figure 16:
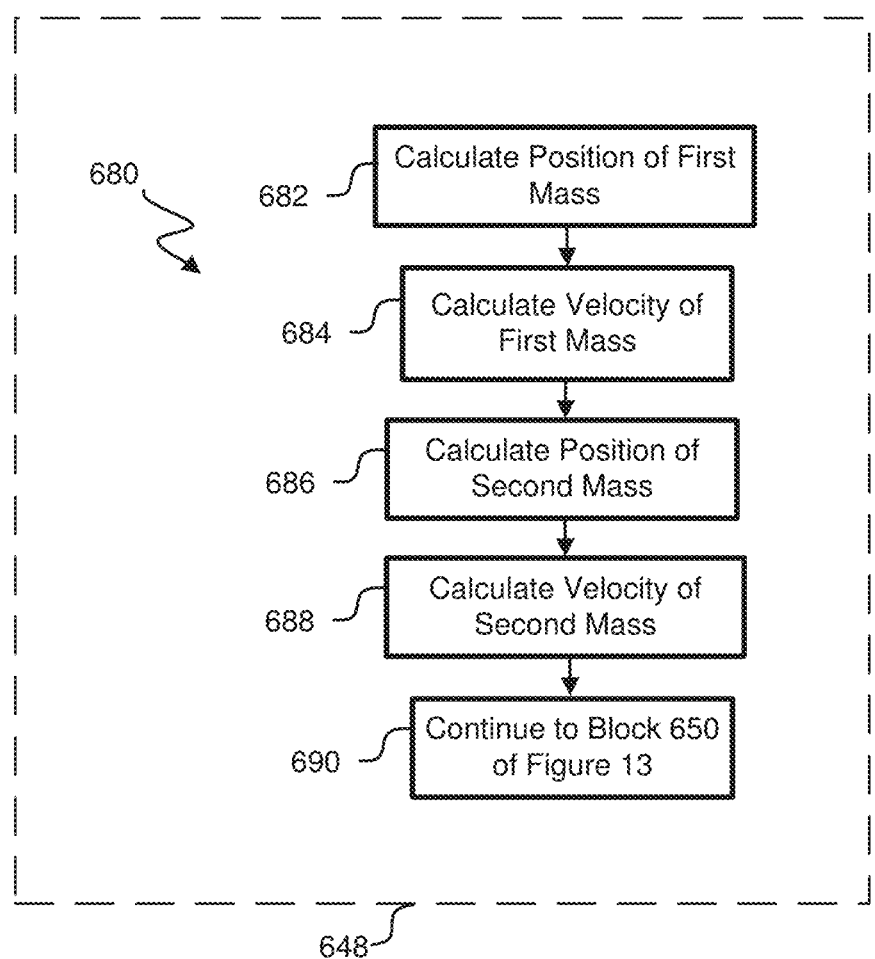
FIG. 16 is a flowchart illustrating one embodiment of a process for calculating a step value.

FIG. 16 is a flowchart illustrating one embodiment of a process for calculating a step value. The process 680 can be performed as part of, or in the place of block 648 of FIG. 13. The process 680 begins at block 682 wherein the next position of the first mass 704 is calculated. In some embodiments, the position of the first mass 704 can be calculated according to the following equation, wherein x1 is the initial position of the first mass 704, v1 is the initial velocity of the first mass 704, T is the duration of a time period such as, for example, the duration of a servo time step, and x1' is the next position of the first mass 704.

$$x1'=v1*T+x1$$

After the next position of the first mass 704 has been calculated, the process 680 proceeds to block 684 wherein the next velocity of the first mass 704 is calculated. In some embodiments, the next velocity of the first mass 704 can be calculated according to the following equation, wherein v1 is the initial velocity of the first mass 704, v2 is the initial velocity of the second mass 706, b1 is the damping coefficient of the first dashpot 708, b2 is the damping coefficient of the second dashpot 712 and v1' is the next velocity of the first mass 704.

$$v1'=v1-b1*v1-b2*v1+b2*v2$$

After the next velocity of the first mass 704 has been calculated, the process 680 proceeds to block 686 wherein the next position of the second mass 706 is calculated. In some embodiments, the next position of the second mass 706 can be calculated according to the following equation, wherein x2 is the initial position of the second mass 706, v2 is the initial velocity of the second mass 706, T is the duration of a time period such as, for example, the duration of a servo time step, and x2' is the next position of the second mass 706.

$$x2'=v2*T+x2$$

After the next position of the second mass 706 has been calculated, the process 680 proceeds to block 688 wherein the next velocity of the second mass 706 is calculated. In some embodiments, the next velocity of the second mass 706 can be calculated according to the following equation, wherein v1 is the initial velocity of the first mass 704, v2 is the initial velocity of the second mass 706, b1 is the damping coefficient of the first dashpot 708, b2 is the damping coefficient of the second dashpot 712 and v2' is the next velocity of the second mass 706.

$$v2'=v2+b2*v1+b2*v2$$

In some embodiments, steps 682-688 can be performed by the processor 58 or other component of the MIRS system 10. After the velocity of the second mass 706 has been calculated, the process 680 proceeds to block 690 and continued with block 650 shown in FIG. 13.

Figure 17A:
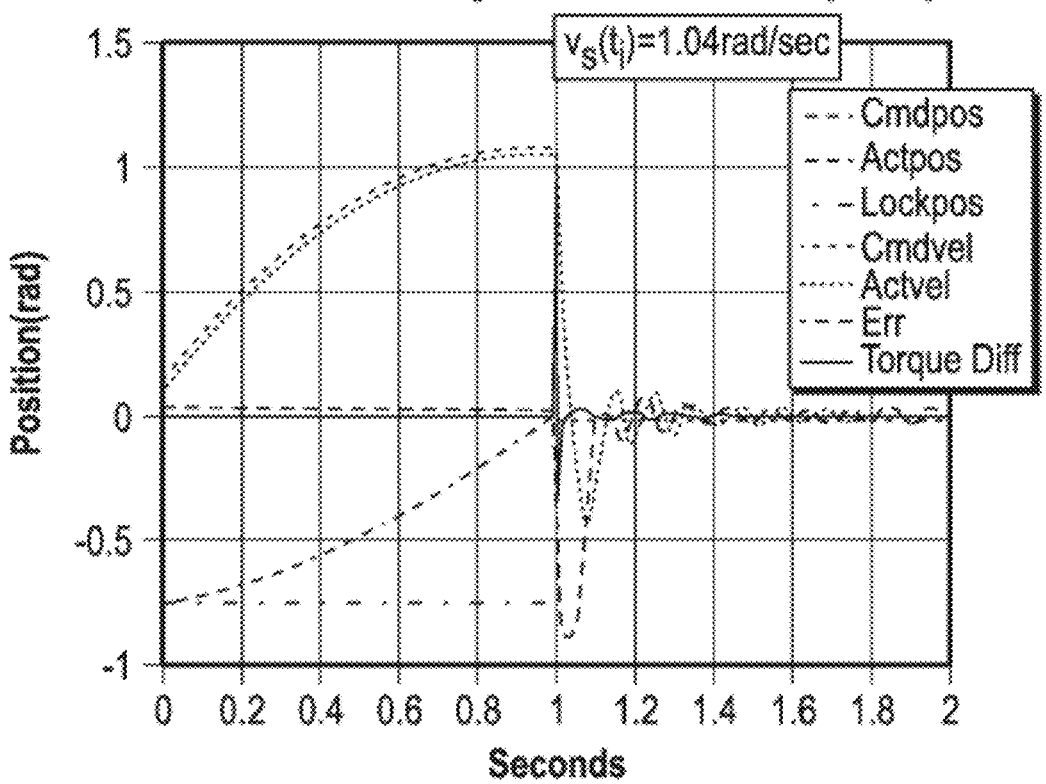
FIGS. 17A-17B show a comparison of results when command shaping to dampen vibrations is used with results when command shaping to dampen vibrations is not used.
Figure 17A:
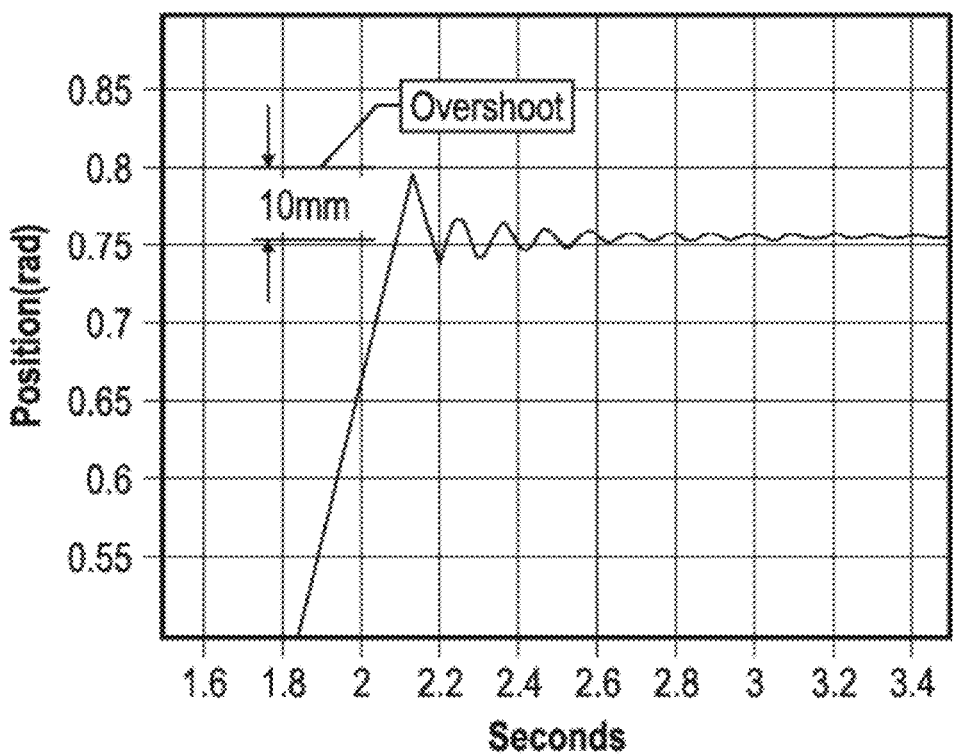
Figure 17B:
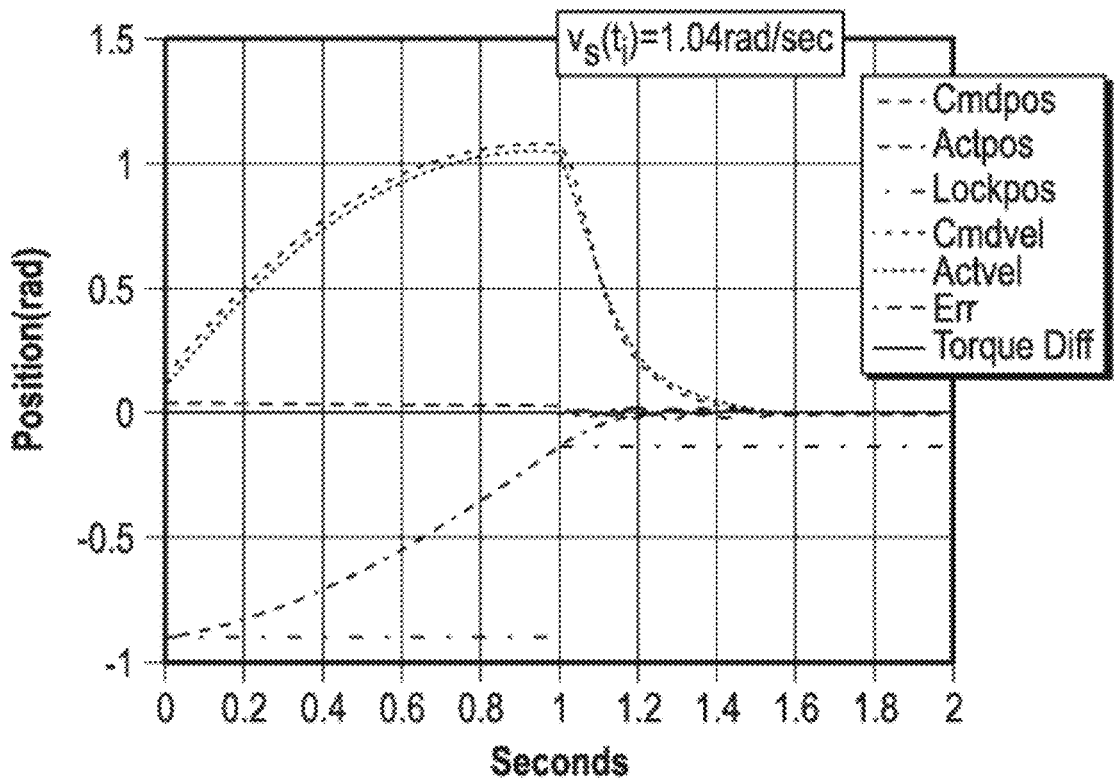
Figure 17B:
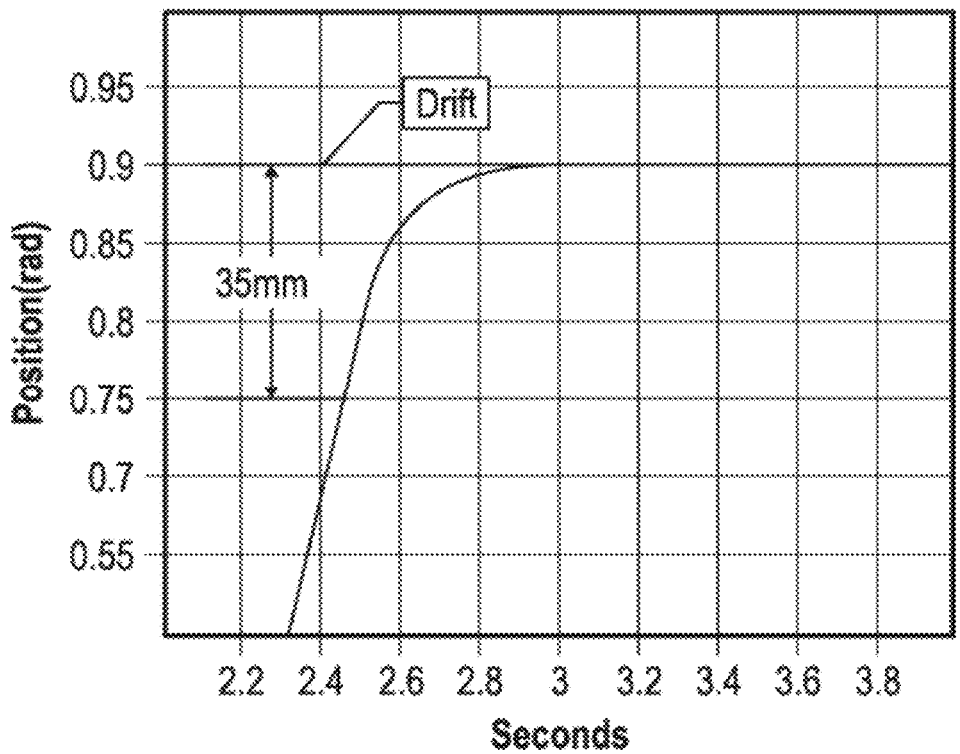

FIGS. 17A and 17B show a comparison of results when command shaping to dampen vibrations is used with results when command shaping to dampen vibrations is not used. The plots in FIG. 17A depict an abrupt mode transition as occurs without the smoothing described herein, and the plots in FIG. 17B depict a smooth mode transition as occurs with the smoothing described herein.

With reference to FIG. 17A, in the plot titled "Takeoff and Landing of Pitch DOF, Case: 5 (Servo)" data measured inside of the MRS system 10 is depicted. The plot includes a trace labeled "Cmdpos" which identifies command position as a function of time, a trace labeled "Actpos" which identifies the actual position of a portion of the MIRS system 10 as a function of time, a trace labeled "Lockpos" which identifies the instant of mode transition and the desired final position of the portion of the MRS system 10, a trace labeled "Cmdvel" which identifies command velocity as a function of time, a trace labeled "Actvel" which identifies the actual velocity of the portion of the MRS system 10 as a function of time, a trace labeled "Err" which identifies the difference between the traces Cmdpos and Actpos as a function of time, and a trace labeled "Torque Diff" which identifies the derivative of torque applied by the one or several motors of the MRS system 10 as a function of time. Although all of the traces are depicted having the same scale, the trace Err does not have the same scale as the others as it has been enlarged to clearly show oscillation in the actual position of the portion of the MRS system 10.

In the plot labeled "Takeoff and Landing of Pitch DOF, Case: 5 (Polaris)" data measured external to the MIRS system 10 is depicted. Specifically, the data depicted in the plot labeled "Takeoff and Landing of Pitch DOF, Case: 5 (Polaris)" was generated with an external measurement device. The data in the plot "Takeoff and Landing of Pitch DOF, Case: 5 (Polaris)" depicts the actual position of a portion of the MIRS system 10 as a function of time. This data in the plot labeled "Takeoff and Landing of Pitch DOF, Case: 5 (Polaris)" corresponds to the trace Actpos in the plot labeled "Takeoff and Landing of Pitch DOF, Case: 5 (Servo)."

As seen in FIG. 17A, oscillation arises due to the mode transition occurring at t=1. These oscillations are evident in all of the traces relating to actual position and velocity of the portion of the MIRS system 10. As seen in FIG. 17A, failure to use command shaping as outlined herein can result in overshoot and vibration. In the particular depicted embodiment, the failure to use command shaping as outlined herein resulted in an overshoot of approximately 10 mm for a component having an initial velocity of 1.04 radians/second. This overshoot is measured as the distance between the desired stopping point (located at 0.75 radians) and the maximum displacement beyond the desired stopping point.

With reference to FIG. 17B, in the plot titled "Takeoff and Landing of Pitch DOF, Case: 15 (Servo)" data measured inside of the MIRS system 10 is depicted. The plot includes a trace labeled "Cmdpos" which identifies command position as a function of time, a trace labeled "Actpos" which identifies the actual position of a portion of the MIRS system 10 as a function of time, a trace labeled "Lockpos" which identifies the instant of mode transition and the desired final position of the portion of the MRS system 10, a trace labeled "Cmdvel" which identifies command velocity as a function of time, a trace labeled "Actvel" which identifies the actual velocity of the portion of the MRS system 10 as a function of time, a trace labeled "Err" which identifies the difference between the traces Cmdpos and Actpos as a function of time, and a trace labeled "Torque Diff" which identifies the derivative of torque applied by the one or several motors of the MRS system 10 as a function of time. Although all of the traces are depicted having the same scale, the trace Err does not have the same scale as the others as it has been enlarged to clearly show oscillation in the actual position of the portion of the MRS system 10.

In the plot labeled "Takeoff and Landing of Pitch DOF, Case: 15 (Polaris)" data measured external to the MIRS system 10 is depicted. Specifically, the data depicted in the plot labeled "Takeoff and Landing of Pitch DOF, Case: 15 (Polaris)" was generated with an external measurement device. The data in the plot "Takeoff and Landing of Pitch DOF, Case: 15 (Polaris)" depicts the actual position of a portion of the MIRS system 10 as a function of time. This data in the plot labeled "Takeoff and Landing of Pitch DOF, Case: 15 (Polaris)" corresponds to the trace Actpos in the plot labeled "Takeoff and Landing of Pitch DOF, Case: 15 (Servo)."

As seen in FIG. 17B, use of command shaping as outlined herein eliminated the vibration shown in FIG. 17A. Specifically, as seen in the plot labeled "Takeoff and Landing of Pitch DOF, Case: 15 (Polaris)," the position smoothly approaches a stable value (in the figure, 0.9 radians). In this embodiment, the use of command shaping as disclosed herein has created a smoothing curve that is C3 continuous, and thus has no discontinuities in jerk. As further seen in the plot labeled "Takeoff and Landing of Pitch DOF, Case: 15 (Polaris)," the use of command shaping as outlined herein eliminates overshoot, but results in drift, and specifically in the depicted embodiment, a drift of approximately 35 mm for a component having an initial velocity of 1.04 radians/second. This drift is measured as the distance between the desired stopping point (located at 0.75 radians) and the maximum displacement beyond the desired stopping point. Surprisingly, however, while the use of command shaping herein results in a drift that is significantly larger than the overshoot created when no command shaping as disclosed herein is used, the use of command shaping as disclosed herein provides better clinical results and provides the user a greater feeling of control of the MIRS system 10.

Further, in some embodiments, the damping coefficients for the first and second dashpots 708, 712 can be manipulated to create different outcomes. Thus, in one embodiment, certain damping coefficients may result in significant overshoot and minimum drift, and in other embodiments, certain damping coefficients can lead to minimum overshoot and significant drift. Advantageously, the combination of certain damping coefficients can yield desirable clinical and/or control outcomes. Similarly, it has been found that, in some embodiments, when the ratio of drift to overshoot is approximately 1.5:1, 2.5:1, 3:1, 3.5:1, 4:1, 5:1, or any other intermediate ratio, clinical outcomes and surgeon experience is maximized. In one embodiments, these ratios can be achieve, for example, by a damping coefficient for the first dashpot 708 of b1=3 and by a damping coefficient for the second dashpot 712 of b2=1.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system comprising:
   a robotic mechanism, wherein the robotic mechanism is moveable; and
   a processor configured to control the robotic mechanism, wherein the processor is configured to:
   detect a request for a mode transition, wherein the request for the mode transition designates a new mode that is different than a current mode;
   determine initial parameters of the robotic mechanism, wherein the initial parameters comprise a position and a velocity of the robotic mechanism;
   calculate a smoothing curve, wherein the smoothing curve transitions between the current mode and the new mode; wherein the smoothing curve has no discontinuities in velocity, acceleration, and jerk; and
   move the robotic mechanism according to the smoothing curve.

2. The system of claim 1, wherein the processor is further configured to identify a degree of freedom of the robotic mechanism affected by the mode transition.

3. The system of claim 2, wherein the processor is further configured to calculate a smoothing curve for the identified degree of freedom.

4. The system of claim 1, wherein to calculate the smoothing curve, the processor is configured to:
establish a first command position;
calculate a step value; and
set a second command position based on the first command position and the step value.

5. The system of claim 4, wherein the second command position comprises the first command position incremented by the step value.

6. The system of claim 4, wherein the processor is further configured to:
determine whether additional smoothing is desired; and
when additional smoothing is desired:
establish a third command position; and
calculate a second step value.

7. The system of claim 6, wherein the third command position is set to the second command position.

8. The system of claim 1, wherein the initial parameters further comprise an acceleration parameter.

9. The system of claim 1, wherein to determine the request for the mode transition, the processor is configured to determine whether smoothing of the mode transition is indicated.

10. The system of claim 9, wherein the processor is configured to determine whether smoothing of the mode transition is indicated by determining whether estimated vibrations from the mode transition exceed a threshold value.

11. The system of claim 9, wherein to determine whether smoothing of the mode transition is indicated, the processor is configured to:
determine post-mode-transition parameters of the robotic mechanism, wherein the post-mode-transition parameters comprise a position and a velocity of the robotic mechanism after the mode transition;
determine a difference between the initial parameters and the post-mode-transition parameters; and
compare the difference between the initial parameters and the post-mode-transition parameters to a threshold.

12. The system of claim 11, wherein the processor is further configured to terminate calculation of the smoothing curve in response to receiving a second request for a mode transition.

13. A method comprising:
detecting, by a processor, a request for a mode transition, wherein the request for the mode transition designates a new mode that is different than a current mode of a robotic mechanism;
determining, by the processor, initial parameters of a portion of the robotic mechanism, wherein the initial parameters comprise a position and a velocity of the portion of the robotic mechanism;
calculating, by the processor, a smoothing curve, wherein the smoothing curve transitions between the current mode and the new mode, and wherein the smoothing curve has no discontinuities in velocity, acceleration, and jerk; and
moving, by the processor using one or more actuators, the portion of the robotic mechanism according to the smoothing curve.

14. The method of claim 13, wherein calculating the smoothing curve comprises:
establishing a first command position;
calculating a step value; and
setting a second command position using the first command position and the step value.

15. The method of claim 14, further comprising:
determining, by the processor, whether additional smoothing is desired; and
when additional smoothing is desired:
establishing, by the processor, a third command position; and
calculating, by the processor, a second step value.

16. The method of claim 13, wherein the smoothing curve comprises a plurality of iteratively calculated steps.

17. The method of claim 16, wherein the calculating of the smoothing curve is terminated in response to receiving a second request for a mode transition.

18. The method of claim 13, wherein the initial parameters further comprise an acceleration parameter.

19. A non-transitory computer-readable medium comprising a plurality of instructions which when executed by a processor are adapted to cause the processor to perform a method comprising:
detecting a request for a mode transition, wherein the request for the mode transition designates a new mode that is different than a current mode of a robotic mechanism;
determining initial parameters of a portion of the robotic mechanism, wherein the initial parameters comprise a position and a velocity of the portion of the robotic mechanism;
calculating a smoothing curve, wherein the smoothing curve transitions between the current mode and the new mode, and wherein the smoothing curve has no discontinuities in velocity, acceleration, and jerk; and
moving, using one or more actuators, the portion of the robotic mechanism according to the smoothing curve.

20. The non-transitory computer-readable medium of claim 19, wherein calculating the smoothing curve comprises:
establishing a first command position;
calculating a step value; and
setting a second command position using the first command position and the step value.

* * * * *

UNITED STATES PATENT AND TRADEMARK OFFICE
CERTIFICATE OF CORRECTION

PATENT NO. : 10,939,969 B2
APPLICATION NO. : 16/204449
DATED : March 9, 2021
INVENTOR(S) : Nitish Swarup and David W. Robinson It is certified that error appears in the above-identified patent and that said Letters Patent is hereby corrected as shown below:

On the Title Page

(63) Related U.S. Application Data:
Please delete "Continuation of application No. 15/125,944, filed as application No. PCT/US2015/020875 on Mar. 17, 2015, now Pat. No. 10,201,390." and insert --Continuation of application No. 15/125,944, filed on Sep. 13, 2016, now Pat. No. 10,201,390, which is a 371 of application No. PCT/US2015/020875, filed on Mar. 17, 2015.--.

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*